United States Patent [19]

Nelson et al.

[11] Patent Number: 4,873,481

[45] Date of Patent: Oct. 10, 1989

[54] MICROWAVE RADIOMETER AND METHODS FOR SENSING ATMOSPHERIC MOISTURE AND TEMPERATURE

[75] Inventors: Loren D. Nelson, Morrison; Lee A. Erb; Randolph H. Ware, both of Boulder; Donald Rottner, Littleton, all of Colo.

[73] Assignee: Radiometrics Corporation, Littleton, Colo.

[21] Appl. No.: 156,614

[22] Filed: Feb. 16, 1988

[51] Int. Cl.[4] .................... G01W 1/02; G01W 1/08
[52] U.S. Cl. ........................ 324/58.5 R; 324/58.5 A
[58] Field of Search .......... 324/58 R, 58.5 R, 58.5 A, 324/58 A, 95; 73/336.5

[56] References Cited

U.S. PATENT DOCUMENTS

| | | | |
|---|---|---|---|
| 2,964,703 | 12/1960 | Sargent et al. | 324/95 |
| 3,327,212 | 7/1967 | Taub et al. | 324/95 |
| 3,409,827 | 11/1968 | Gogging, Jr. | 324/58.5 A |
| 3,693,095 | 9/1972 | Wilt | 324/58.5 R |
| 3,911,435 | 10/1975 | Mardon et al. | 324/344 |

FOREIGN PATENT DOCUMENTS 1078111  8/1967  United Kingdom .......... 324/58.5 R

OTHER PUBLICATIONS

Hogg, David C., et al, "An Automatic Profiler of the Temperature Wind and Humidity in the Troposphere", *Journal of Climate and Applied Meteorology*, vol. 22, May, 1983, pp. 807-831.

Hogg, David C., et al., "A Steerable Dual-Channel Microwave Radiometer for Measurement of Water Vapor and Liquid in the Troposphere", *Journal of Applied Meteorology*, vol. 22, May 1983, pp. 789-806.

Jansenn, M. A., "A New Instrument for the Determination of Radio Path Delay Variations Due to Atmospheric Water Vapor", *IEEE Transactions on Geoscience and Remote Sensing*, vol. GE-23, Jul., 1985, pp. 485-490.

Hogg, David C., et al, "An Antenna for Dual-Wavelength Radiometry at 21 and 32 GHz", *IEEE Transactions on Antennas and Propagation*, vol. AP-27, No. 6, Nov. 1979, pp. 764-771.

Stacey, J. M., *Spaceborne Receivers, Basic Principles*, JPL Publications 84-89, Dec. 1, 1984, pp. 46,50 and 51.
Stacey, J. M., *Microwave Blackbodies for Spaceborne Receivers*, JPL Publication 85-10, Mar. 1, 1985, p. 22.
Wheeler, Gershon J., *Introduction to Microwaves*, (Prentice-Hall, 1963) pp. 6-15.
Guiraud, Fred O., "A Dual-Channel Microwave Radiometer for Measurement of Precipitable Water Vapor and Liquid", *IEEE Transactions on Geoscience Electronics*, vol. GE-17, No. 4, Oct., 1979, pp. 129-136.

*Primary Examiner*—Reinhard J. Eisenzopf
*Assistant Examiner*—Maura K. Regan
*Attorney, Agent, or Firm*—Rothgerber, Appel, Powers & Johnson

[57] ABSTRACT

A passive, multi-channel microwave radiometer includes an antenna-lens assembly for receiving, and a first waveguide designed to provide a common path for propagating, 23.8 GHz and 31.4 GHZ atmospheric signals. The 23.8 GHz signal is above the frequency of relative maximum water vapor absorption and the 31.4 GHz signal is near a relative minimum in the water vapor absorption spectrum. Circuitry is responsive to the atmospheric signals for generating output signals representing the respective water vapor and liquid content in and the temperature of the atmosphere. For realtime calibration a blackbody assembly is mounted in the near field of the antenna-lens assembly. The blackbody assembly emits known blackbody microwave signals at 23.8 GHz, 31.4 GHz and in the V band. The radiometer is calibrated during its normal operation by causing a mirror to select the blackbody signals for propagation along the common path. The circuitry responds to the blackbody signals to represent them as first blackbody reference signals. A factory calibrated noise diode assembly adds a known noisy microwave signal to the first waveguide when a blackbody signal is being processed. The circuitry separately responds to such combined blackbody and noisy signals to separately generate a second blackbody reference signal. These first and second blackbody reference signals and the known temperature of the blackbody assembly are used to provide realtime calibration data that is used in realtime to obtain the output signals in response to the atmospheric signals.

37 Claims, 8 Drawing Sheets

MICROWAVE RADIOMETER AND METHODS FOR SENSING ATMOSPHERIC MOISTURE AND TEMPERATURE

BACKGROUND OF THE INVENTION

1. Field of the Invention

This invention relates to sensing passive microwave energy and more particularly to passive microwave radiometry apparatus and methods for indicating atmospheric water vapor content, liquid content and temperature.

2. Description of the Prior Art

Microwave radiometers are generally known as passive broad-band receivers that collect radiation emitted from a surface. In the past, microwave radiometers have been designed for response to selected portions of the microwave spectrum according to the function to be performed by the radiometer. For meteorological applications, the 22 GHz region has been identified for determining atmospheric water vapor using the 22.235 GHz water vapor resonance line. 60 GHz is another meteorological region for determining atmospheric temperature profiles based on thermal emission from oxygen.

In the past, the collected signals of a microwave radiometer have been recorded as amplitude-time histories which are related to an absolute temperature reference. As of 1976 temperature sensitivities of ±0.05 degrees Kelvin (herein noted as "K") rms were said to be possible, but it was reported that due to size, weight and power limitations, compromises were necessary in applying microwave radiometers to particular applications. Such applications of passive microwave radiometers include measuring total water vapor content, liquid water content and refractive index properties of the atmosphere.

These quantities are typically inferred from passive microwave measurements of the sky brightness temperature at a plurality of microwave and millimeter wave frequencies having different water vapor and liquid water absorption coefficients. Typical "dual-channel" systems use two frequencies, one at about 22.4 GHz and the other at about 31.4 GHz. The 22.4 GHz frequency corresponds to the peak of a broad water vapor absorption line and 31.4 GHz frequency is near a relative minimum in the water vapor absorption spectrum. At these frequencies, absorption and re-radiation due to liquid water aerosols obey Rayleigh's scattering theory. Their attenuation (dB/Km) thus varies as the inverse square of the wavelength in this spectral region. Absorption is stronger in the 31.4 GHz region than at the 22.4 GHz region if liquid water is present. Ice particles are effectively transparent at both frequencies, whereas water vapor absorbs more strongly near 22.4 GHz than at 31.4 GHz.

The microwave absorption coefficients of water vapor and liquid water clouds vary as a function of frequency in this spectral range. The attenuation at 22.4 GHz caused by a fixed amount of water vapor (e.g. 1 gram per cubic meter over a 1 kilometer path length) increases with increasing altitude. However, at certain frequencies above and below 22.4 GHz such attenuation decreases with increasing altitude. As a result, the attenuation curves (attenuation vs. frequency) for different altitudes cross each other at a pressure invariant frequency on each side of 22.4 GHZ. Such pressure invariant frequencies are at about 20.6 GHz and about 24.1 GHz. These crossing points can be referred to as pressure invariant or crossover points on the attenuation vs. frequency curves. The attenuation caused by a fixed amount of cloud liquid water droplets (e.g. 0.1 gram per cubic meter over a 1 kilometer path length) does not peak in the same spectral range, but does vary with changing altitude.

In their *Journal of Climate and Applied Meteorology* article at Vol. 22: pp. 789-806, May, 1983, entitled "A Steerable Dual-Channel microwave Radiometer for Measurement of Water, Vapor and Liquid in the Troposphere", D. C. Hogg and others ("Hogg B") selected two frequencies, 20.6 GHz and 31.6 GHz, for water vapor and liquid measurements. A separate radiometer was used for each frequency and they were located in a single package that provided an essentially constant temperature environment for the radiometers and the antenna.

The oxygen microwave absorption band in the 60 GHz region of the spectrum was discussed in the same issue of the *Journal of Climate and Applied Meteorology*. In an article entitled "An Automatic Profiler of the Temperature, Wind and Humidity in the Troposphere", at pp 807-831, Hogg and others ("Hogg B") discuss the use of this band to measure the temperature profile of the atmosphere. Since oxygen is a well mixed gas of known concentration, changes in oxygen band sky brightness indicate different temperatures of the atmosphere above the antenna. Multiple oxygen band wavelengths and/or multiple antenna look angles allow temperature profiles to be retrieved since they have different attenuation and thus different spatial weightings of radiating gas temperature.

Known experimental prototypes using known methods to measure true "sky brightness temperature" are subject to drift in gain and offset are expensive power consumptive, and not easily portable. For example in Hogg B a heat pump is used to stabilize the temperature of a housing of a trailer that contains the radiometer system. Similarly, a building is shown in Hogg A for housing the radiometers, radar receivers and other equipment. Also, in an article by M. A Janssen entitled "A New Instrument For The Determination of Radio Path Delay Due To Atmospheric Water Vapor", 1985, *IEEE Transactions on Geoscience and Remote Sensing.* GE-23:485-490, a smaller radiometer instrument is shown, but a thermoelectric heat pump is used to maintain the radiometer at a constant temperature.

Differentials between the radiometer temperature and the temperature of the sensed atmosphere present problems to the radiometer designer. On the one hand, sky brightness temperatures typically range from 20K to 150K in the 20 to 35 GHz band. On the other hand, the physical temperature of the antenna and the waveguides of a ground-based radiometer are nominally 300K. Present calibration techniques require frequent "tipping curve" calibrations that use the cosmic background (2.7K) as a calibration standard. As a result, full realtime calibration of the available radiometers is not feasible with present techniques when clouds are present, which is the very condition of greatest meteorological interest.

If all physical radiometer components are ideal and have neither resistive losses, impedance mismatch, nor thermal self re-radiation of microwave energy, then the transfer function of sky radiance signal power into the receiver is unity. A typical microwave water vapor radiometer-received sky brightness temperature (power) of 50K [$T_{B,sky}$] would appear at the radiometer output as an identical effective output brightness temperature of 50K [$T_{B,out}$]. However, the actual situation is more complex. In particular, DC signal offset appears in radiometers since they use non-ideal microwave antennas and transmission components. For example, where the radiometer components are all ideal except for the microwave horn antenna itself, an antenna dissipative loss of only 0.1 dB corresponds to an antenna fractional loss of [$10^{.1/10} - 1 = 0.023$], or a horn efficiency [$E_{horn}$] of 97.7%. Under these conditions, the Rayleigh-Jeans Approximation and Schwarzchild's Equation can be used to calculate the effective output brightness temperature of the radiometer as:

$$T_{B,out} = [T_{B,sky}][E_{horn}] + T_{horn}[1 - E_{horn}] \quad \text{Eq (1)}$$

If typical values are assumed for:
$T_{B,sky}$ = 50K (for a water vapor radiometer at 23.8 GHz),
$T_{horn}$ = 300K (local ambient temperature), and
$E_{horn}$ = 0.977 (0.1 dB losses);
then, after applying the radiometric transfer function of Eq. 1, the result is:

$$T_{B,\ out} = 55.75K$$

Since this is an overestimate of +5.75K, this offset error is already ten times the amount of a desirable design goal (absolute accuracy level) of 0.5K in sky brightness temperature and appears as a DC offset level in measured sky brightness temperature. The gain drift is −2.3% in this example.

Unfortunately, actual transfer function system offsets are likely to be somewhat worse than the 0.1 dB losses noted above. For example, Stacey, in *Spaceborne Receivers. Basic Principles.* JPL Publication 84-89, Dec. 1, 1984, gives the following breakdown for 0.75 dB in hypothetical radiometer total internal losses:

$L_f$ = 0.1 dB (feedhorn losses)
$L_{wg}$ = 0.2 dB (waveguide losses)
$L_{sw}$ = 0.3 dB (modulator switch losses)
$L_i$ = 0.15 dB (isolator losses)

Repeating the analysis of Eq. 1 with such 0.75 dB internal losses under the same conditions indicates that a sky brightness temperature of 50K would be sensed at the radiometer output as 97.125K. To keep this offset error within the design goal of 0.5K the above analysis indicates that the front end antenna losses, according to Eq. 1, can be no more than 0.2% or 0.008 dB.

Prior physical hardware are not this accurate. For example, Stacey, in *Microwave Blackbodies for Spaceborne Receivers,* JPL Publication 85-10, 1985), found that dissipative losses in high quality corrugated horn antennas are about 0.2 dB. Wheeler, in his book *Introduction to Microwaves,* (Prentice Hall, 1963), gave theoretical formulas for dissipative losses in copper waveguide. For size WR34 rectangular waveguide at an operating frequency of 23.8 GHz, a theoretically ideal Waveguide would have dissipative losses of 0.144 dB/foot. Thus, by the above analysis, 0.7 inches of waveguide at 300K would cause a 0.5K sky brightness error. Similar tiny loss mismatch in waveguide switches will destroy absolute accuracy in switched hot-loads in the waveguide path. Non-dissipative voltage standing wave ratio (VSWR) mismatch in waveguide paths also destroys absolute accuracy.

In summary, prior art passive radiometers must be calibrated at frequent intervals using the tipping curve technique, even though such technique depends on clear skies for accuracy. Further, based on these calculations using the characteristics of prior art passive radiometers, it appears that switched hot-loads in the waveguide path do not give an accurate absolute calibration by themselves. Nonetheless, the prior art regards switched hot-loads as absolute brightness temperature sources referenced to the antenna input since their absolute temperature is known. In reality, in applicants experiences, lossy microwave components cause both gain and offset drift of the transfer function. Finally, to avoid drift of the transfer function the Prior art radiometers consume power necessary to maintain them at a constant temperature.

SUMMARY OF THE INVENTION

Applicants have re-evaluated prior dual channel radiometers in an endeavor to minimize the noted limitations. As a result, in contrast to the prior art the present invention avoids constant temperature requirements, minimizes the effects of waveguide losses during calibration, and avoids the use of tipping curve calibrations during normal use by providing a portable, low-power multichannel radiometer method and apparatus.

An object of the present invention is to provide a microwave radiometer and method to allow full internal gain and offset autocalibration without regular use of tipping curves.

Another object of the present invention is to provide an atmospheric water radiometer that is portable, light weight, low in power consumption, and relatively low in cost.

A further object of the present invention is to achieve relatively narrow angular antenna beamwidths at distinct wavelengths in a very small physical package by using a microwave antenna-lens assembly.

A still further object of the present invention is to combine both V and K band microwave energy from a single antenna-lens assembly and to split such energy to direct the two bands simultaneously to two separate receivers without the use of any waveguide switches or diplexers.

A related object of the present invention is to provide an atmospheric water vapor radiometer with a radome designed to permit all weather operation and minimize sky brightness temperature errors due to radome losses.

Yet another object of the present invention is to allow realtime calibration of both gain and offset of a radiometer at both 23.8 and 31.4 GHz by means of the combined use of an external physical microwave blackbody placed upstream of the antenna assembly and a noise diode coupled into a single waveguide by high attenuation cross-waveguide couplers.

It is a further object of the present invention to eliminate the routine need for tipping curve calibrations of a radiometer by substituting physical blackbody and noise diode calibrations for ongoing tipping curve calibrations, to allow calibration during inclement weather and cloudy skies when use of tipping curve calibration is not practical.

An additional object of the present invention is to eliminate the need for thermostatic temperature control of a radiometer enclosure by intermittently referencing the calibrations in real time to a physical blackbody placed upstream of an antenna-lens assembly to eliminate any gain and offset drift errors caused by imperfect waveguide reradiation that varies over temperature and any gain drift of the receiver that varies over temperature.

A Yet additional object of the present invention is to use selected radiometer measurement frequencies that are optimum for measuring atmospheric water substance content, that are also free from the possibility of man-made microwave interference, and that allow use of a single waveguide for propagating signals having such selected frequencies.

A still additional object of the present invention is to allow simultaneous measurement of sky brightness temperature in the 50–60 GHz oxygen absorption band through the same antenna-lens assembly and along the same single microwave signal path as is used for the selected water substance measurement, with such 50–60 GHz band being separated from the water substance band using a wire-grid polarizer rather than waveguide switches or diplexers.

With these and other objects in mind, a multi-channel, passive microwave radiometer for determining the water vapor content and the liquid content in the atmosphere includes an antenna for receiving atmospheric signals having frequencies substantially in two separate ITU protected bands. A first frequency is above the frequency of relative maximum water vapor absorption and a second frequency is near a relative minimum in the water vapor absorption spectrum. The radiometer includes circuity responsive to the received atmospheric signals at the first and second frequencies for generating output signals representing such water vapor and liquid content in the atmosphere from which the atmospheric signals were received.

Another feature of a passive microwave radiometer of the present invention includes a feed horn having a relatively small aperture area for receiving microwave signals within a broadband containing both first and second frequencies. The first frequency is above the frequency of relative maximum water vapor absorption and the second frequency is near a relative minimum in the water vapor absorption spectra. A unit is provided for receiving microwave signals in the K and V bands and for focusing such signals within such broadband, including the first and that second frequencies, into the feed horn. A unitary waveguide propagates the microwave signals received from the feed horn within such broadband, including the first and second microwave frequencies. Significantly, the bandpass of the unitary waveguide is wide enough to pass both the first and second frequencies because the first frequency is selected to be above the frequency of relative maximum water vapor absorption. A blackbody is mounted adjacent an aperture of the receiving unit for emitting known blackbody microwave signals having frequencies in the K and V bands. A mirror selectively reflects microwave signals from the atmosphere and from the blackbody into the aperture of the receiving unit so that the first and second signals and the blackbody signals are propagated through the same length of each of the receiving unit, the feed horn and the waveguide to render the blackbody signals effective to form an accurate reference for measuring K and V band atmospheric signals, including those at the first and second frequencies.

A method according to the principles of the present invention determines the water vapor content and the liquid content in the atmosphere. The method includes the steps of guiding in a common path such microwave signals as are received from the atmosphere and as have selected, first and second microwave frequencies. The first frequency is selected to be above the microwave frequency of relative maximum water vapor absorption and the second frequency is selected to be near a relative minimum in the microwave water vapor absorption spectra. Such guiding is followed by responding alternately to the first and second frequency signals in the common path and generating first and second output signals representing respectively the water vapor content and the liquid content of the atmosphere from which the microwave signals were received.

Another aspect of the method according to the principles of the present invention determines at least one selected characteristic of the atmosphere from a location on the earth. The method includes the steps of providing a housing adapted to be hand carried to such location for defining a volume. Blackbody microwave signals within a band corresponding to the selected characteristic are emitted into the volume. Next, microwave signals from the atmosphere are admitted into the volume. Then the atmospheric signals and the blackbody signals are selectively propagated along a common path. A first reference signal is generated in response to the blackbody signals. A predetermined noise signal is then added to the blackbody signals in the common path to generate a second reference signal, and the first and second reference signals form calibration data. Before the atmospheric signals are propagated in the common path, the noise signal is stopped so that the common path propagates the selected atmospheric signals without the added noise signals. In response to the atmospheric signals, a first output is generated and is compared to the calibration data to generate a second output representative of the selected characteristic of the atmosphere.

BRIEF DESCRIPTION OF THE DRAWINGS

Other objects, features and advantages of the present invention will be apparent from an examination of the following detailed descriptions, which include the attached drawings in which.

DETAILED DESCRIPTION OF THE PREFERRED EMBODIMENT

Microwave Absorption Coefficients

Figure 1A:
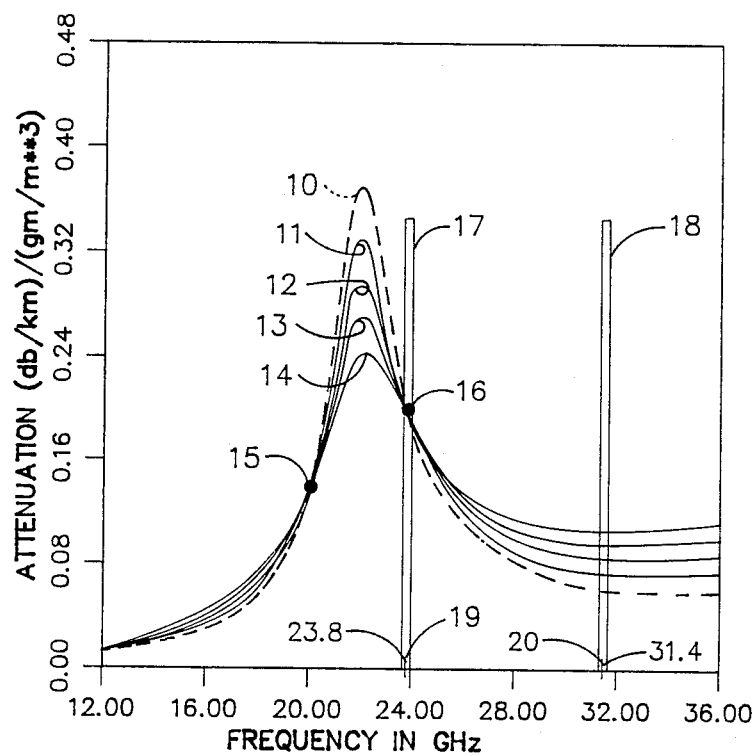
FIG. 1A is a graph illustrating the microwave attenuation coefficient of atmospheric water vapor as a function of measurement frequency.
Figure 1B:
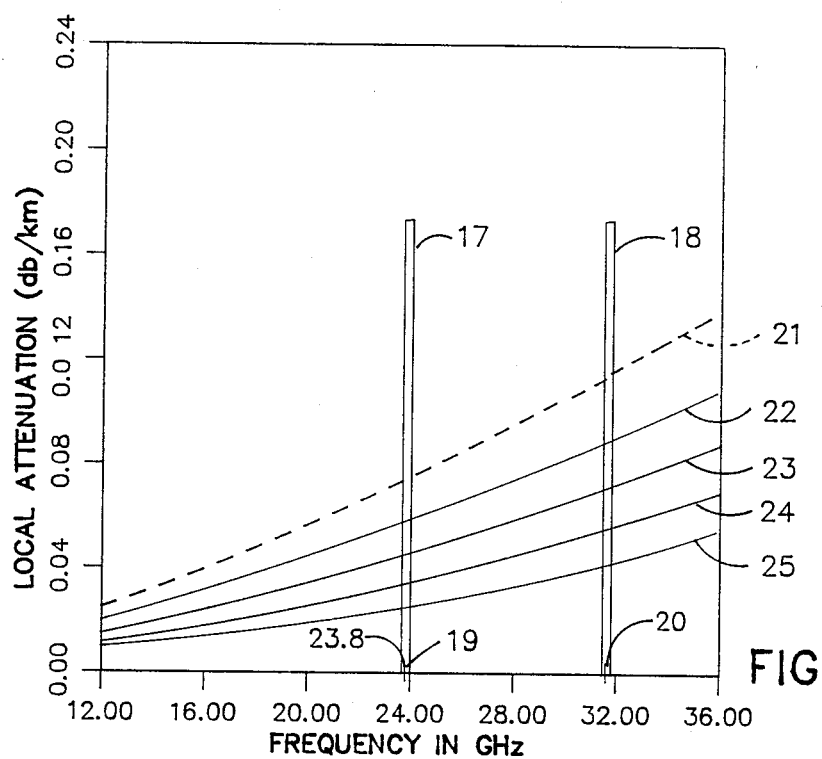
FIG. 1B is a graph illustrating the microwave attenuation coefficient of liquid water in clouds as a function of measurement frequency.

A general understanding of microwave absorption coefficients may be had by referring to FIGS. 1A and 1B. In FIG. 1A the microwave spectral range from 12 GHz to 36 GHz is shown and attenuation is indicated in (db/km)/(gm/m3), where "gm/m3" indicates grams per meter cubed. FIG. 1A illustrates the attenuation caused by a fixed amount of water vapor (1 gram per cubic meter over a 1 kilometer path length) at various altitudes in the U.S. standard atmosphere. Curves 10, 11, 12, 13, and 14 in FIG. 1A are respectively for 600, 700, 800, 900 and 1000 Mb pressures. FIG. 1A also shows crossover, or pressure invariant, points 15 and 16 at which the respective curves 10 through 14 intersect. In prior art radiometers, the crossover point 15 at 20.6 GHz has been selected as the frequency at which atmospheric radiation is sensed for processing since the attenuation at the crossover point 15 is independent of altitude. Thus, atmospheric signals having a 20.6 GHz frequency are typically sensed in prior art radiometers. FIG. 1A also shows the second crossover point 16 as being on the upper frequency side of the peaks of the various curves 10 through 14, and being at a frequency of about 23.8 GHz.

Further, FIG. 1A shows a pair of International Telecommunication Union ("ITU") frequency bands 17 and 18, respectively. The first band 17 has a frequency range from 23.60 to 24.00 GHz and the second band 18 has a frequency range of 31.3 to 31.5 GHz. These bands are internationally protected regions where, by agreement of the International Telecommunication Union, no active terrestrial microwave radiation sources are allowed.

According to the principles of the present invention, a first frequency 19 is selected to be in or adjacent the ITU band 17 and at or near the second crossover point 16. This first frequency 19 has the advantage of being in or so closely adjacent the ITU band 17 that it is relatively free from man-made atmospheric radiation. Also, since the frequency 19 is adjacent the second crossover point 16, there is relatively little attenuation with varying altitude from which the sensed radiation was emitted. Other advantages of selecting the 23.8 GHz frequency 19 are discussed below. A second 31.4 GHz frequency 20 is used as the second frequency since it is within the ITU band 18 and there is relatively low attenuation with respect to atmospheric water vapor.

Referring now to FIG. 1B, the ITU bands 17 and 18 are shown along with curves 21 through 25 illustrating the variation in attenuation (in db/km) caused by a fixed amount of cloud liquid water droplets (0.1 gram per cubic meter over a 1 kilometer path length) at various altitudes in the U.S. standard atmosphere. With increasing altitude, the attenuation increases as indicated by the curve 21 at high elevation and the curve 25 at low elevation, for example. The points on the curves 21–25 at the 23.8 GHz liquid water frequency 19 are relatively weak as compared to the points on the curves 21–25 at the 31.4 GHz frequency

SUMMARY OF THE PREFERRED EMBODIMENT

Figure 4:
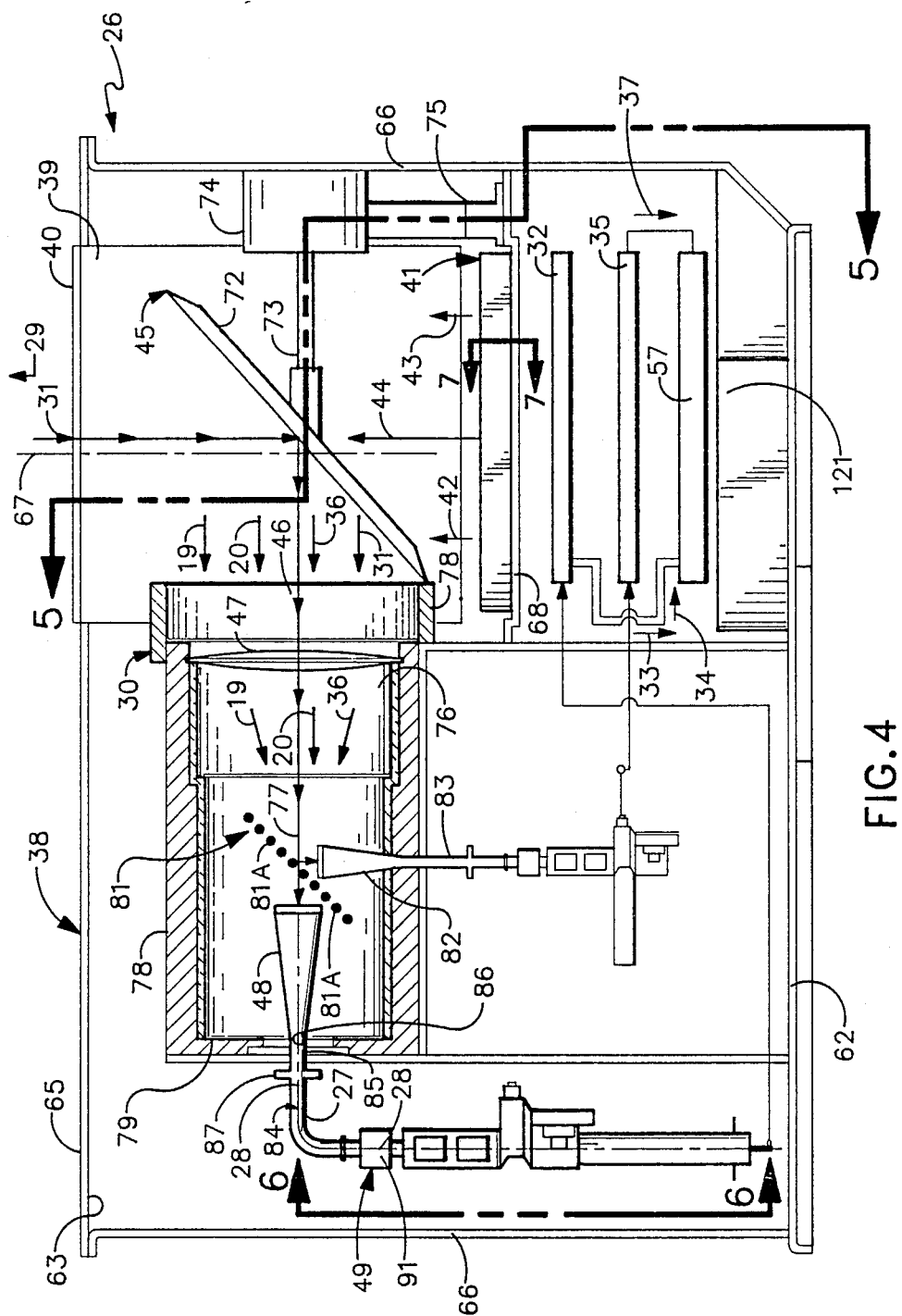
FIG. 4 is a side elevational view of a preferred embodiment of the passive microwave radiometer of the present invention showing a mirror for selectively directing atmospheric signals and blackbody signals into an antennalens assembly.

Referring now to FIG. 4 a passive, multi-channel microwave radiometer 26 is shown including a first waveguide 27. The first waveguide 27 is designed to provide a common path 28 for propagating both the 23.8 GHz signal 19 and the 31.4 GHz signal 20, which avoids use of two separate waveguides as in the prior art. In greater detail, the multi-channel, passive microwave radiometer 26 is used for determining the water vapor content and the liquid content in the atmosphere 29. The radiometer 26 includes an antenna-lens assembly 30 for receiving the 23.8 GHz signal 19 and the 31.4 GHz signal 20 among other broadband signals 31 received, for example, from the atmosphere 29. As noted above, the 23.8 GHz signal 19 is above the frequency of relative maximum water vapor absorption and the 31.4 GHz signal 20 is near a relative minimum in the water vapor absorption spectrum shown in FIG. 1A. The radiometer 26 includes circuitry 32 responsive to the atmospheric signals 19 and 20 for generating output signals depicted by an arrow 33 and an arrow 34. The arrow 33 denotes output signal 33A and the arrow 34 represents an output signal 34A representing the respective water vapor and liquid content in the atmosphere 29 from which the atmospheric signals 19 and 20 were received. The radiometer 26 also includes additional circuitry 35 for indicating the temperature of the atmosphere 29 in response to V band signals 36 from the atmosphere 29 and generates output signals 37A (depicted by an arrow 37) representing the temperature of the atmosphere 29.

The radiometer 26 of the present invention may be contained in a relatively portable housing 38 having a first section 39. A microwave signal transparent window or radome 40 is provided in the first section 39 of the housing 38 for receiving the broadband atmospheric signals 31, including the 23.8 and 31.4 GHz signals 19 and 20, respectively, and the V band signals 36.

Realtime Calibration Structure

Figure 3:
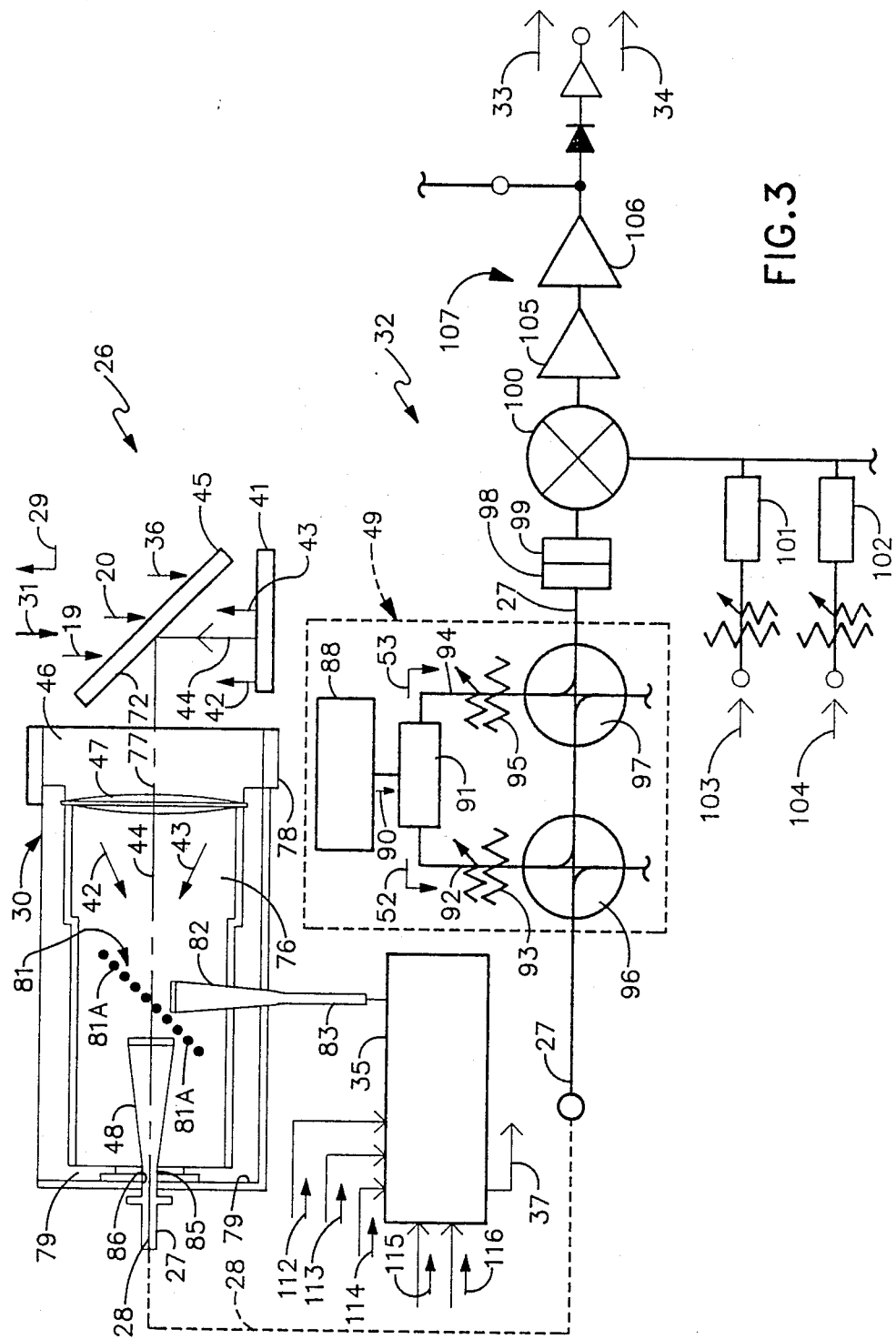
FIG. 3 is a schematic diagram of the passive microwave radiometer according to the present invention, which performs the methods of the present invention for determining characteristics of the atmosphere.

Referring also to FIG. 3, for realtime calibration a blackbody assembly 41 is mounted in the first section 39 in the near field of the antenna-lens assembly 30. The assembly 41 emits known blackbody microwave signals, including blackbody signals 42 at 23.8 GHz, blackbody signals 43 at 31.4 GHz and V band blackbody signals 44 at 52.8, 53.8, 55.4 and 58.9 GHz A mirror unit 45 is operated for selectively directing into an aperture 46 of the antenna-lens assembly 30 the broadband signals 31 (FIG. 4) and the blackbody signals 42 through 44 (FIG. 3). As shown in FIG. 4, the 23.8 and 31.4 GHz signals 19 and 20 are focused by a lens 47 of the antenna-lens assembly 30 into a feed horn antenna 48 coupled to the first waveguide 27. As shown in FIG. 3, the 23.8 and 31.4 GHz signals 42 and 43 are focused by the lens 47 into the feed horn antenna 48. Since the first waveguide 27 is designed to propagate both the first and second 23.8 and 31.4 GHz signals such signals are propagated along the common path 28 whether they have been received as the respective signals 19 and 20 as a part of the atmospheric signals 31 or from the blackbody assembly 41 as the respective blackbody signals 42 and 43.

Realtime Calibration Method.

The radiometer 26 is calibrated during its normal broadband operation by causing the mirror unit 45 (in position one, see FIG. 3) to select the blackbody signals 42 and 43, which are focused by the lens 47 into the feed horn antenna 48 and then propagated along the common path 28 by the first waveguide 27. The circuitry 32 is effective to respond to the blackbody signals 42 and 43 at the 23.8 and 31.4 GHz frequencies and to represent them, respectively, as first output blackbody reference signals 33R1 and 34R1 (see respective arrows 33 and 34).

Referring now to FIG. 3, with the mirror unit 45 still selecting the blackbody signals 42 and 43, a noise diode assembly 49 is operated. The noise diode assembly 49 has previously been calibrated, such as before shipment of the radiometer 26, using a tipping curve 50 (FIG. 2A) that is used to obtain a first linear transfer function 51 (FIG. 2B). Based on such preliminary calibration, the noise diode assembly 49 adds a known noisy microwave signal 52 to the first waveguide 27 when the 23.8 GHz blackbody signal 42 is being processed. The noise diode assembly 49 is also effective to add a known noisy microwave signal 53 to the first waveguide 27 when the 31.4 GHz blackbody signal 43 is being processed. The circuitry 32 separately responds to the combined blackbody signal 42 and the noisy signal 52, and to the combined blackbody signal 43 and the noisy signal 53, to separately generate a second output blackbody reference signal 33R2 at the 23.8 GHz frequency and a second output blackbody reference signal 34R2 blackbody at the 31.4 GHz frequency, respectively, illustrated by the respective arrows 33 and 34.

Referring to FIG. 2B, since these respective first and second output blackbody reference signals 33R1 and 33R2, and 34R1 and 34R2 (for the respective 23.8 and 31.4 GHz frequencies) are known, and since, as discussed below, the temperature $T_{BB}$ of a blackbody 54 (FIG. 7) in the blackbody assembly 41 is known, the change in brightness temperature "delta $T_{ND}$" resulting from the noise diode assembly 49 can then be determined from the first linear transfer function 51. Delta $T_{ND}$ may be used to plot respective second and third linear transfer functions 55 and 56 (FIG. 2C).

Figure 2A:
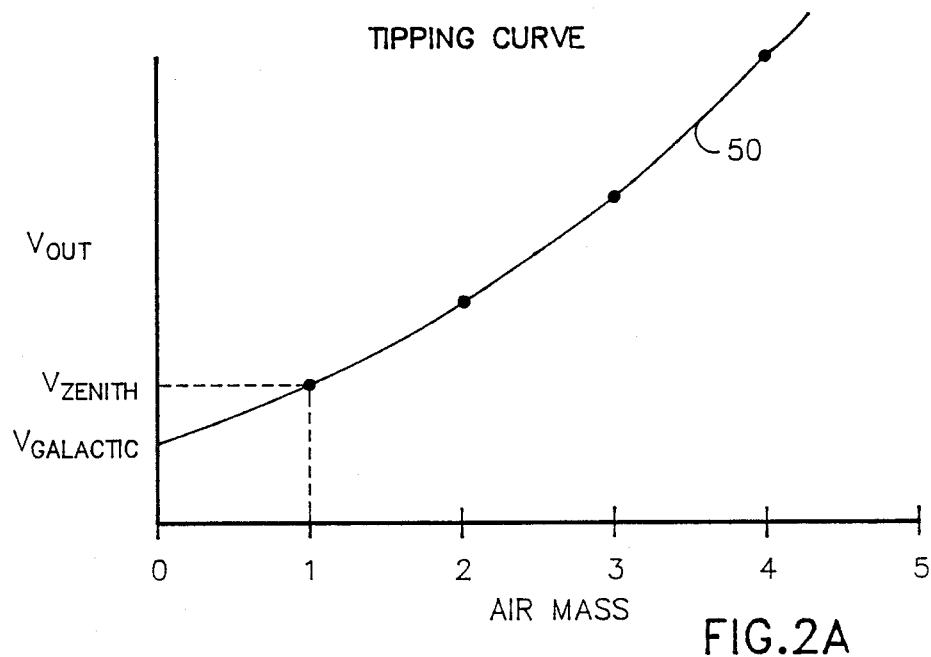
FIG. 2A is a tipping curve graph used in factory calibration of the radiometer of the present invention, showing $V_{galactic}$ obtained from the tipping curve.
Figure 2B:
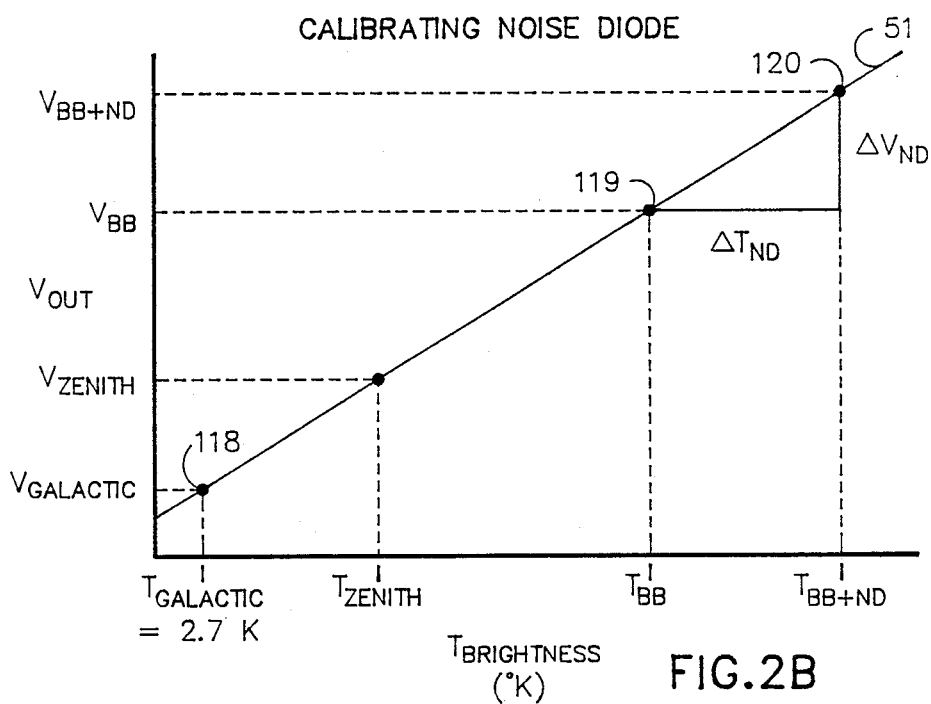
FIG. 2B is a linear transfer function graph based on known ($V_{galactic}$, $T_{galactic}$) and ($V_{BB}$, $T_{BB}$) points for obtaining a value for the delta $T_{ND}$ resulting from operation of a noise diode that is used for realtime calibration of the radiometer of the present invention.
Figure 2C:
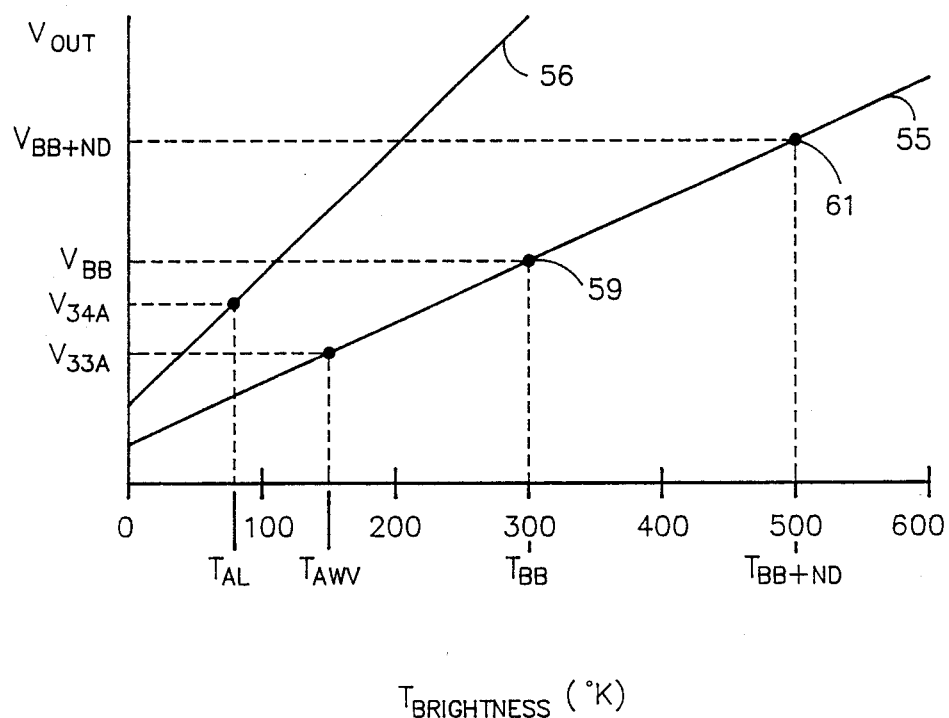
FIG. 2C is a linear transfer function graph based on known ($V_{BB}$, $T_{BB}$) and ($V_{BB+ND}$, $T_{BB+ND}$) points obtained in realtime using the method and radiometer of the present invention, by which an output $V_A$ derived from the atmosphere is used to determine the atmospheric brightness temperature $T_A$.
Figure 8:
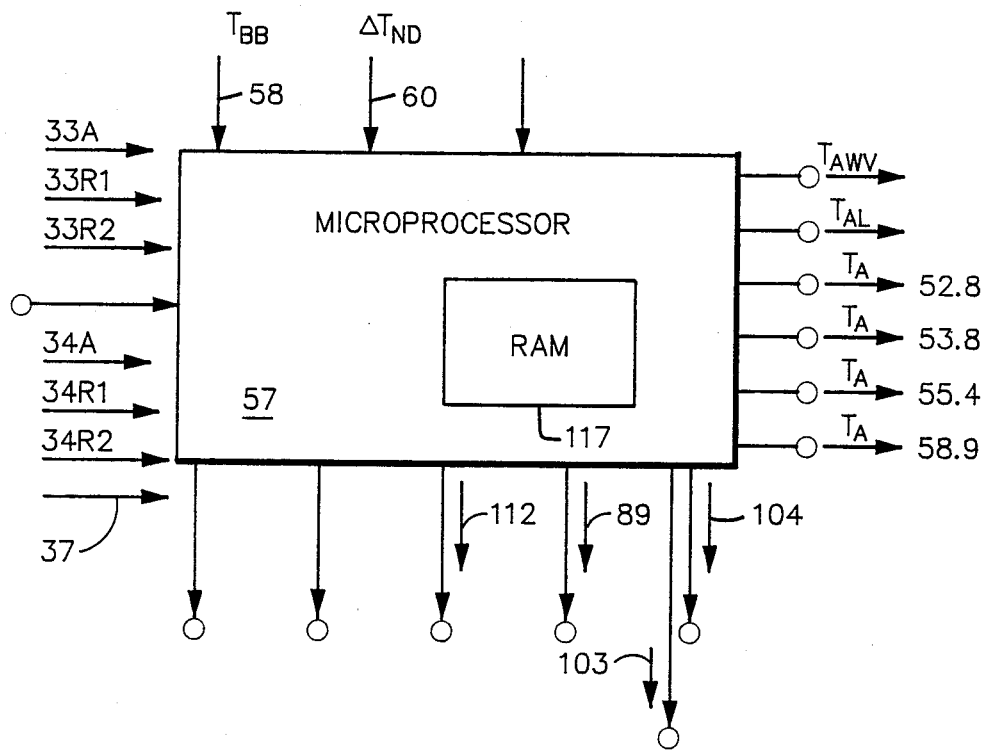
FIG. 8 is a block diagram of a processor that controls the operation of the radiometer and generates output signals representing the water vapor content, the liquid content and the temperature in the atmosphere.

Referring to FIGS. 2C and 8, these are plotted in terms of a given output voltage ($V_{OUT}$ and a known brightness temperature (T) in K. In particular, the first blackbody reference signal 33R1 appears as a voltage $V_{BB}$ (shown in FIG. 2C) and is input to a processor 57 (FIG. 8). As discussed below, the blackbody temperature $T_{BB}$ is known, and it is input to the processor 57 as a signal 58. The processor 57 thus has the voltage and temperature data for a ($V_{BB}$,$T_{BB}$) point 59 in FIG. 2C. Similarly, the second blackbody reference signal 33R2 appears as a voltage $V_{BB+ND}$ shown in FIG. 2C and is input to the processor 57. Since delta $T_{ND}$ is known, and is input to the processor 57 as a signal 60, the processor 57 adds $T_{BB}$ to $T_{ND}$ to produce $T_{BB+ND}$. Thus, the data for a ($V_{BB+ND}$, $T_{BB+ND}$) point 61 (FIG. 2C) is known. The processor 57 draws the second linear transfer function 55 using the points 59 and 61. The function 55 represents realtime calibration data. The radiometer 26 is then ready to take readings from the atmosphere 29.

Reatime Atmospheric Sensing Apparatus

For realtime atmospheric sensing, the mirror unit 45 is adjusted to a second position (shown in FIG. 4). The broadband atmospheric signals 31 admitted to the first section 39 of the housing 38, including the signals 19 and 20, are reflected into the antenna-lens assembly 30 and are focused by the lens 47 into the common path 28 of the first waveguide 27. With the signal 19 selected for processing by the circuitry 32 FIG. 3), the 23.8 GHz output signal 33A is generated in the form of a given $V_{OUT}$ (see the arrow 33). The output signal 33A is supplied to the processor 57 (FIG. 8), which uses the second linear transfer function 55 (FIG. 2C) to determine the brightness temperature $T_{AWV}$ (FIG. 2C) that corresponds to $V_{33A}$, which represents the water vapor content of the atmosphere 29 from which the signal 19 was received.

After selecting the 31.4 GHz signal 20 from the common path 28, in a similar manner the circuitry 32 then generates the 31.4 GHz output signal 34A (see the arrow 34 in FIGS. 3 and 4 and $V_{34A}$ in FIG. 2C) and it is applied to the processor 57. The processor 57 uses the third linear transfer function 56 (FIG. 2C) to determine the brightness temperature $T_{AL}$ that corresponds to $V_{34A}$, which in the form of brightness temperature represents the liquid content of the atmosphere 29 from which the signal 20 was received. It should be understood that in each case the output signals 33A and 34A are based on both atmospheric water vapor and liquid. However, because of the substantially different absorption of water vapor and liquid at 23.8 GHz and 31.4 GHz, the resulting $T_{AWV}$ and $T_{AL}$ can represent the respective water vapor content and liquid content of the atmosphere 29. In this sense, then, the output signals 33A and 34A are said to represent the respective water vapor content and liquid content of the atmosphere 29.

Realtime Atmospheric Sensing Methods

A method of the present invention provides data representing the water vapor content and the liquid content of the atmosphere 29. The method includes the steps of receiving the atmospheric signals 19 and 20 and positioning the mirror unit 45 to reflect such atmospheric signals 19 and 20. The reflected signals 19 and 20 are focused and propagated along the common path 28. The 23.8 GHz signal 19 is selected for processing. In response to the 23.8 GHz signal 19, the output signal 33A (arrow 33) is generated and by referring to the second linear transfer function 55 (FIG. 2C) the output voltage $V_{33A}$ is used to determine the corresponding brightness temperature $T_{AWV}$, which represents the water vapor content of the atmosphere 29 from which the signal 19 was received.

In a second operational cycle, the method further includes the steps of generating the output signal 34A in response to the 31.4 GHz signal 20. In a manner similar to the use of the output signal 33A, the output signal 34A is used with the third linear transfer function 56 (FIG. 2C) to determine the corresponding brightness temperature $T_{AL}$, such that the output signal 34A (arrow 34) is representative of the liquid content of the atmosphere 29 from which the signal 20 was received.

Realtime Calibration Method

Referring to FIGS. 2B and 3, another method of the present invention provides realtime calibration to provide the second and third linear transfer functions 55 and 56 without realtime use of a tipping curve and without controlling the temperature of the structure of the radiometer 26. The method includes the steps of selecting the blackbody 54 (FIG. 7) so as to emit the first 23.8 GHz blackbody signal 42, the second 31.4 GHz blackbody signal 43 and the V band blackbody signals 44. These blackbody signals 42, 43 and 44 are propagated in the common path 28. In a first realtime calibration cycle, the first blackbody signal 42 is processed to form the first blackbody reference signal 33R1 (see the arrow 33) and then the corresponding noisy signal 52 is added to generate the second blackbody reference signal 33R2. The first and second blackbody reference signals 33R1 and 33R2, and the delta $T_{ND}$ are used to produce the second linear transfer function 55 (FIG. 2C).

In a second realtime calibration cycle, the second blackbody signal 43 is processed to generate the first blackbody reference signal 34R1 (see the arrow 34R1 in FIG. 8) and then the corresponding known noisy signal 53 is added to generate the second blackbody reference signal 34R2. The first and second blackbody reference signals 34R1 and 34R2, and the delta $T_{ND}$ are used to produce the third linear transfer function 56 (FIG. 2C).

Detailed Description of Radiometer 26

Figure 5:
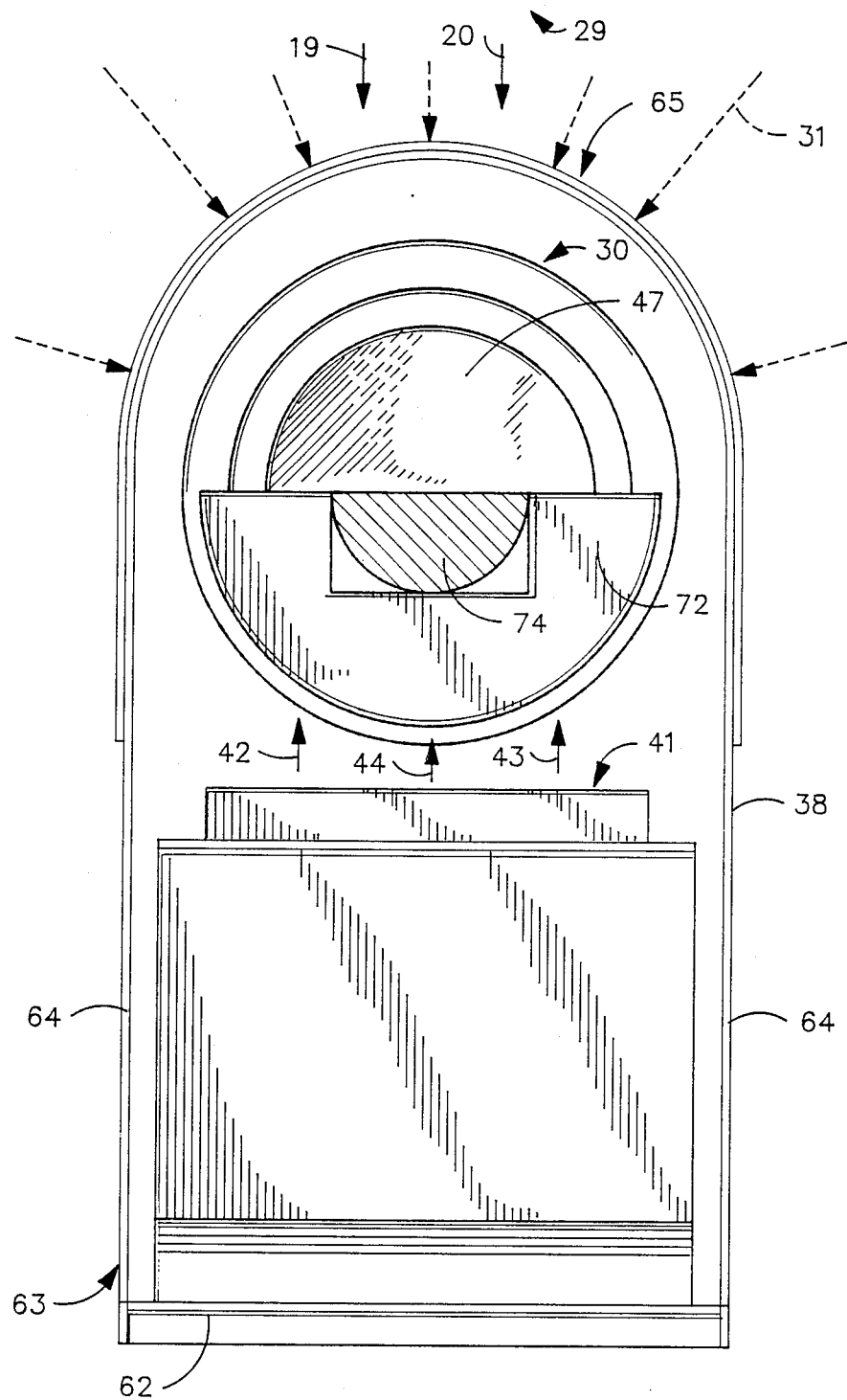
FIG. 5 is an end view taken along the line 5—5 in FIG. 4 showing the antenna-lens assembly feeding signals at 23.8 and 31.4 GHz into a common path in a first waveguide shown in FIG. 4.

The multi-channel passive microwave radiometer 26 is shown in FIGS. 4 and 5 as including the housing 38. The housing 38 is formed from a bottom 62 that supports a cover 63 having opposite sides 64—64 that extend upwardly and curve inwardly to form a curved top 65. Opposite ends 66—66 close the housing 38 and protect the structure of the radiometer 26 from moisture, for example, in the atmosphere 29. The bottom 62, sides 64—64, ends 66—66 and top 65 of the housing 38 form an electromagnetic radiation shield, but are not, however, thermally insulated. Thus, changes in temperature in the atmosphere 29 are readily conducted through the housing 38. As indicated above, the radiometer 26 is intended to be relatively portable. For this purpose, in a preferred embodiment the radiometer 26 is about 27 inches long (FIG. 4), less than 10 inches wide (FIG. 5) and about 18 inches high.

In FIG. 4 the first section 39 of the housing 38 is shown provided with the window or radome 40 formed in the top 65. The window 40 is preferably formed from Teflon material which is nearly transparent to the broad band microwave signals 31 that are radiated along a vertical axis 7 from the atmosphere 29 If desired, a hydrophobic surface film may be applied to the outside of the window 40 to promote beading and runoff of liquid water, which would material attenuate the incoming atmospheric signals 31. As shown in FIG. 4, opposite the window 40 a horizontal support or shelf 68 is provided for supporting the blackbody assembly 41.

Figure 7:
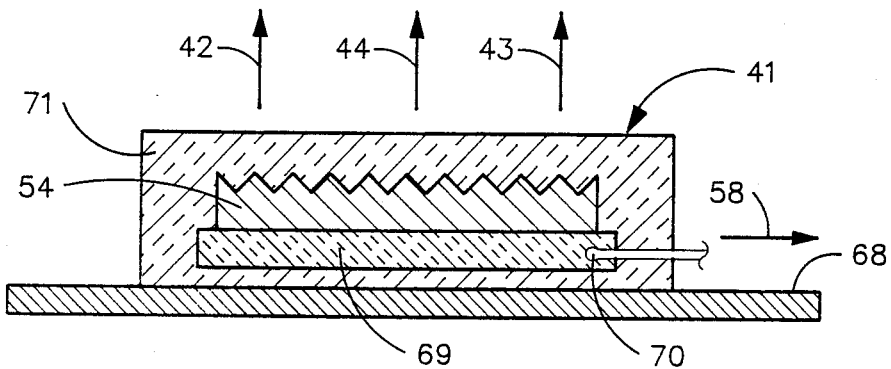
FIG. 7 is a cross-sectional view taken along line 7—7 in FIG. 4 showing a blackbody used for realtime calibration of the radiometer.

Referring to FIG. 7, the blackbody assembly 41 includes the blackbody 54 supported on a first side of a thermally conductive plate 69. The blackbody 54 is selected to emit relatively broadband blackbody signals, including at least the signals 42 through 44 at the respective 23.8 and 31.4 GHz K band frequencies and within the V band. The blackbody signals 42 through 44 represent a known temperature as measured by a thermometer 70 that is embedded in the plate 69. The thermometer 70 is connected to the processor 57 (FIG. 8) and generates the $T_{BB}$ signal 58.

Since the housing 38 is not insulated against thermal transfer, the temperature within the housing 26 will vary with that of the local ambient atmosphere 29 outside of the housing 38. An insulating layer 71 surrounds the assembly formed by the blackbody 54, the plate 69 and the thermometer 70 for limiting the rate of heat transfer to the blackbody 54, the plate 69 and the thermometer 70 such that the temperature of the blackbody 54 will be nearly isothermal. The insulation layer 71 is, however, transparent to microwave signals, such as the signals 42, 43 and 44, and may be formed from a foam material of low microwave dielectric constant, such as Emerson Cummings ECHOFOAM PP material.

Referring to FIGS. 3–5, the mirror unit 45 is mounted between the blackbody 54 on the shelf 68 and the window 40 within the first section 39 of the housing 38. As mounted on the shelf 68, the blackbody assembly 41, including the blackbody 54, is in the near field of the antenna-lens assembly 30. The mirror unit 45 includes a mirror 72 that reflects microwave signals in the 20 to 60 GHz range. The mirror 72 is mounted on a horizontal shaft 73 that is supported on and rotated by a stepping motor 74 mounted on a vertical bracket 75. The stepping motor 74 is controlled to rotate the shaft 73 and position the mirror 72 iu various positions. The first position is shown in FIG. 3. In the first position, the broadband atmospheric radiation 31 admitted to the first section 39 of the housing 38 is reflected and does not enter the antenna-lens assembly 30. However, the blackbody radiation, such as the blackbody signals 42 through 44, are reflected at 90 degrees and enter the aperture 46 of the antenna-lens assembly 30 that is received in a second section 76 of the housing 38. The motor 74 is also controlled to rotate the shaft 73 to move the mirror 72 into other angular positions, including the second position shown in FIG. 4. There, the zenith broadband atmospheric signals 31 are reflected into the antennalens assembly 30. Thus, depending upon whether the mirror 72 is positioned in the first or second position, either the blackbody signals 42 through 44 or the zenith broadband atmospheric signals 31 are reflected into the aperture 46 of the antenna-lens assembly 30. The stepping motor 74 can be controlled to position the mirror 72 at angular positions between the second position (zenith) and 90 degrees off the second position, which is the azimuth position.

As shown in FIG. 4, the antenna-lens assembly 30 includes the lens 47 that has a longitudinal axis 77 that extends generally perpendicular to the vertical axis 67 of incoming atmospheric signals 31 and the blackbody signals 42-44 before reflection off the mirror 72. The lens 47 is provided with a relatively small diameter (such as six inches) and may be convex (as shown) or plano-convex in configuration. In a preferred embodiment, the lens 47 is made of Rexolite brand material, having a microwave refractive index different from that of air, and is planoconvex with a radius of curvature of 4.88 inches. The lens 47 is specifically designed to focus the 23.8 GHz signals and the 31.4 GHz signals from either the atmosphere 29 (respective signals 19 and 20) or the blackbody 54 (respective signals 42 and 43). The signals 19 and 20 are focused toward the longitudinal axis 77 as they propagate through a collar 78 toward the feed horn antenna 48. The lens 47 also focuses the V band signals 36 towards the longitudinal axis 77. The collar 78 is lined with a microwave absorber material, such as Keene Corporation's ML-73 graded index absorber, to suppress side-lobes of the focused microwave signals 19 and 20. In this manner, the beam width of the antenna-lens assembly 30 is small and has sharp fall off at the edges of the beam.

Between the aperture 46 of the assembly 30 and a closed end 79 of the collar 78, a wire-grid polarizer 81 is supported at a 45 degree angle to the longitudinal axis 77. The polarizer 81 is effective to deflect some of the incoming microwave signals downwardly at right angles to the longitudinal axis 77. The wires 81A—81A of the polarizer 81 are nominally 1 mm in diameter and are at nominally 2.5 mm intervals. The deflected signals may be the broadband atmospheric signals 31 or the blackbody signals 42 through 44, for example. The deflected signals are received by a second feed horn antenna 82 connected to a second waveguide 83. The second feed horn antenna 82 and the second waveguide 83 are designed for propagating the signals 36 and 44 in the V band for use in indicating the temperature of the atmosphere 29 from which the signals 36 were received.

The first waveguide 27 is coupled to the feed horn antenna 48 and has a central axis 84 that is initially coextensive with the longitudinal axis 77 of the antennalens assembly 30. The central axis 84 forms the common path 28 for the focused 23.8 GHz and 31.4 GHz signals 19 and 20, respectively. As indicated, the 23.8 GHz and 31.4 GHz signals may be received from either the blackbody 54 or the atmosphere 29, depending upon the position of the mirror 72. The first waveguide 27 is sized to be between the size of prior art waveguides for propagating the K and Ka bands. In particular, the internal dimensions of the first waveguide 27 are 0.340 inches by 0.170 inches According to waveguide designation custom, this would be designated as a WR34 waveguide if this size were a standard, commercially available size. With the WR34 dimensions, the TEM(00) mode is propagated for frequencies between 22 and 33 Ghz, such that both of the 23.8 and 31.4 GHz signals 19 and 20, and the signals 42 and 43, respectively, are easily propagated through the first waveguide 27. In contrast, K band waveguides propagate the 18 through 26.5 GHz frequencies and Ka waveguides propagate the 26.5 through 40 GHz frequencies. Thus, prior art radiometers that are designed using the 22.4 GHz and 31.4 GHz frequencies cannot use a single waveguide. In particular, no single waveguide will selectively propagate the TEM(00) mode at both of the 20.6 GHz and 31.4 GHz frequencies. Thus, prior art radiometers have included two separate waveguides, one for 20.6 GHz and one for 31.4 GHz, which requires more space and a separate circuit for processing signals from each waveguide.

The antenna-lens assembly 30, including the feed horn antenna 48, the lens 47 and the above-described absorber material, combine to optimize the reception of the K and V band signals 19, 20 and 36 from the mirror unit 45. The antenna-lens assembly 30 provides single polarization half power full beam width ("HPFBW") nominal 5.7° at 23.8 GHz and HPFBW nominal 4.4° at 31.4 Ghz. The beam widths are approximately equal, being 4.4 degrees and 5.7 degrees. The side lobes are attenuated 25 db at both the 23.8 GHz and 31.4 GHz frequencies and at both the E and H polarizations. The feed horn antenna 48 may be provided with a suitable waveguide stub 85, such as a 2 inch stub, that extends through an aperture 86 in the closed end 79 of the collar 78 to connect with the first waveguide 27. A UG 1530/U flange 87 may be used, for example. The voltage standing wave ratio in the first waveguide 27 is 1.3:1 at both the 23.8 and 31.4 GHz frequencies.

The second feed horn antenna 82 and the second waveguide 83 are similarly designed, except that they propagate the atmospheric V band signals 36 and the 52.8, 53.8, 55.4 and 58.9 GHz blackbody signals 44.

Signal Processing

Figure 6:
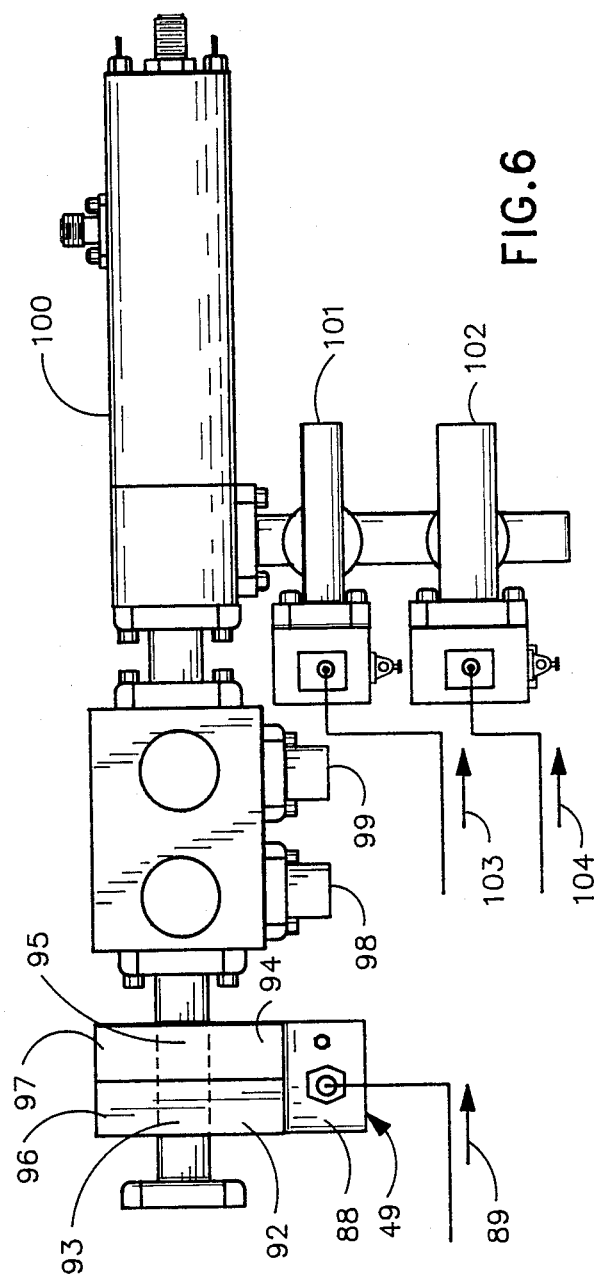
FIG. 6 is a side elevational view of the first waveguide shown in FIG. 4 showing the noise diode coupled to attenuators that feed cross couplers.

Considering the processing of the 23.8 and 31.4 GHz signals 19 and 20, respectively, and referring to FIGS. 3 and 6, the first waveguide 27 extends along and defines the common path 28 (FIGS. 3 and 4) and propagates the signals 19 and 20 first to the noise diode assembly 49. As discussed above, the noise diode assembly 49 is used in the realtime calibration of the radiometer 26. In particular, the noise diode assembly adds to each of the 23.8 and 31.4 GHz blackbody signals 42 and 43, respectively, the respective known noisy signals 52 or 53 at the respective 23.8 or 31.4 GHz frequencies. The noise diode assembly 49 includes a noise diode 88 that is turned on or off by a control signal 89. The noise diode 88 generates a broadband noise signal 90 (FIG. 3 that has a selected amplitude that is to the first order independent of the temperature of the noise diode 88. Thus, as the structure of the noise diode assembly 49 drifts with ambient temperature in the housing 38, the maximum amplitude of the broadband noise signal 90 is nearly constant. The broadband noise signal 90 is split by a splitter 91 (FIGS. 3 and 4) and is fed through a first short waveguide 92 to a 3.8 GHz attenuator 93 and separately through a second short waveguide 94 to a 31.4 GHz attenuator 95. The attenuators 93 and 95 reduce the raw amplitude (nominally equivalent to 10,000K) of the noise diode signal 90 by an amount such that the attenuated known noisy signals 52 and 53 FIG. 3) add to the blackbody signals 42 and 43 that amount of energy that is equal to about 200K in terms of brightness temperature in the graph shown in FIG. 2C. The calibration of the noise diode 88 is described in detail below.

The attenuators 93 and 95 are connected respectively to cross-couplers 96 and 97, each of which has a minimum length so as to introduce a minimum of waveguide losses to the attenuated noisy signals 52 and 53, respectively. The respective 23.8 and 31.4 GHz attenuated noisy signals 52 and 53 are fed from the respective cross couplers 96 and 97 to the first waveguide 27 and are thus added to the respective blackbody signals 42 and 43 with a minimum of distortion due to ambient temperature or waveguide losses.

According to the position of the mirror 72, either the atmospheric signals 19 and 20, or the blackbody signals 42 and 43, are propagated past the cross couplers 96 and 97. After the cross-couplers 96 and 97, the first waveguide 27 is connected to a series connection of two 20 db isolators 98 and 99 that function as diodes to prevent any of the downstream signals from being reflected back into the first waveguide 27. The isolators 98 and 99 are connected to a mixer 100. The mixer 100 receives the atmospheric signals 19 and 20 or the blackbody signals 42 and 43, and when the noise diode 88 is on, also receives the attenuated noisy signals 52 and 53. The mixer 100 functions to select for processing either the 23.8 GHz signals 19 or 42, the latter being with or without the attenuated noise signal 52. Separately, the 31.4 GHz signals 20 or 43, the latter being with or without the attenuated noisy signal 53, may be selected. The mixer 100 includes separate Gunn oscillators 101 and 102, one operated at the 23.8 GHz frequency and the other operated at the 31.4 GHz frequency. The Gunn oscillators 101 and 102 are controlled by respective frequency selection control signals 103 and 104 to function alternately in the well known heterodyne detection technique, such that the output of the mixer 100 is a heterodyne signal in the range of 0–100 mHz and represents the appropriate atmospheric signals 19 or 20 or the blackbody signals 42 and 43, the latter signals 42 and 43 being with or without the attenuated noisy signals 52 and 53. The output of the mixer 100 is fed to a low-noise preamplifier 105 and a post amplifier 106 in a standard IF amplifier circuit 107. The output voltage of the IF amplifier circuit 107 varies from 0 to 1 volt for representing a range of 0 to 500K in sky brightness temperature. As indicated above, depending on what operational cycle is being performed, the IF amplifier circuit 107 generates any of the various signals 33R1, 33R2, 33A, 34R1, 34R2, or 34A represented by respective arrows 33 and 34.

Still referring to FIG. 3, and now considering the second waveguide 83, the V band signals 44 at the 52.8, 53.8, 55.4 and 58.9 GHz frequencies are processed in a similar manner by the circuitry 35. The circuitry includes components similar to the noise diode assembly 49, the isolators 98 and 99, the mixer 100 and the IF amplifier circuit 107 for adding known noisy signals 108–111 (corresponding to the signal 52, for example) at respective 52.8, 53.8, 55.4 and 58.9 GHz to the respective V band signals 44 at those frequencies. This is done in response to the following control signals that are input to the circuitry 35:

CHART I

| Noise Diode Control Signal | Control Signals | | | |
|---|---|---|---|---|
| | Mixer Frequency Selection Control Signal | | | |
| | 52.8 GHz | 53.8 GHz | 55.4 GHz | 58.9 GHz |
| 112 | 113 | 114 | 115 | 116 |

The signal 112 corresponds to the signal 89 (FIG. 6) and the signals 113 through 116 correspond to the signal 103 (FIG. 3), for example. These are applied to the circuit 35 as shown in FIG. 2 under the control of the processor 57 so that the temperature output signal 37 may selectively represent any of the following signals that correspond to the signals output from the circuit 107:

Chart II

| | Signals 37 | | |
|---|---|---|---|
| Frequency (GHz) | Atmospheric Signal 31 | Blackbody Signal 44 | Blackbody Signal 44 plus noisy signal 108–111 |
| 52.8 | X | | |
| 52.8 | | X | |
| 52.8 | | | X |
| 53.8 | X | | |
| 53.8 | | X | |
| 53.8 | | | X |
| 55.4 | X | | |
| 55.4 | | X | |
| 55.4 | | | X |
| 58.9 | X | | |
| 58.9 | | X | |
| 58.9 | | | X |

Processor 57

Referring to FIG. 8, the operation of the radiometer 26 is controlled by the processor 57. The processor 57 is a microprocessor controlled by the computer program shown in Appendix A.

In the preferred embodiment, the microprocessor of the processor 57 is a computer manufactured by Motorola, Model MC68HC11 and a standard native HC 11 assembly language operating system is used to control the microprocessor in conjunction with the computer program shown in Appendix A. Referring to Appendix A, command 1 is an initializing command. This returns the mirror 72 to a known position by controlling the stepping motor 74. In a preferred embodiment, this known position is referred to as "down" which is the first position shown in FIG. 3. Steps 1.a. through e. are then performed, to initialize the circuitry 107 to test a RAM 117 (FIG. 8) of the processor 57, and to test various buses (not shown) within the processor 57. Also, the stepping motor 74 is initialized After the radiometer 26, including the processor 57, has been properly initialized, the second command, an elevation command, is selected. For example, in performing a preliminary or factory) calibration to prepare the tipping curve 50 (FIG. 2A), the elevation command is initially "+90==Up", which will cause the mirror 72 to be in the second position shown in FIG. 4. The elevation command is then decreased by five degree intervals from the +90 through zero settings so that readings can be taken every five degrees. The vertical or +90 reading is the $V_{zenith}$ reading shown in FIG. 2A and the increasing amounts for $V_{OUT}$ for the tipping curve 50 result from the successive lower angle readings.

For the realtime calibration method of the present invention, the elevation command is set for "−90==Down", such that the mirror 72 is in the first position shown in FIG. 3 for directing the blackbody signals 42 through 44 into the aperture 46. Further, when the realtime sensing is performed, then the elevation command is "+90==Up", such that the mirror 72 is positioned in the second position shown in FIG. 4.

The third of the commands is a period command. The period command determines the radio frequency signal integration time, which determines the number of cycles over which the signals 33 or 34 are integrated. For example the time over which any of the signals 33A, 33R1, 33R2, 34A, 34R1, and 34R2 is integrated may be selected in this manner. The other voltages that are measured by sampling for a fixed interval include that of a power supply 121 (FIG. 4) that is either a switching power supply, or in a portable embodiment, a battery.

Command 4 is an ontime command that is used to specify the period or the duration of the noise control signals 89 (FIG. 6) and 112 (Chart I).

Command 5 is to read an analog channel so that the output of the thermometer 70 is read so that the $T_{BB}$ signal 58 is input to the processor 57 (FIG. 8) to indicate the temperature $T_{BB}$ of the blackbody 54 (FIG. 7).

Command 6 is to read the measurement channels, which results in reading the signals 33 and 34 shown in FIG. 3, for example, which are input to the processor 57 in FIG. 8. Command 6 is discussed below in connection with realtime sensing.

Command 7 is provided as a read status command such that at any time the radiometer 26 may be polled to indicate its general status.

Preliminary/Factory Calibration

As indicated above, a preliminary calibration may be done at the factory prior to shipment of the radiometer 26 when clear sky is available. The factory calibration procedure is summarized as follows:

Chart III

| | Factory Calibration Procedure. |
|---|---|
| Item 1. | Turn on 23.8 GHz Gunn diode 101. |
| Item 2. | Perform tipping curve determination (in clear weather). |
| Item 3. | Find $V_{OUT}$ for $T_{galactic}$. |
| Item 4. | Point to the blackbody 54. |
| Item 5. | Read $T_{BB}$. |
| Item 6. | Measure radiometer output voltage (signal 33A) to obtain $V_{BB}$. |
| Item 7. | Plot points ($T_{BB}$, $V_{BB}$) and ($T_{galactic}$, $V_{galactic}$). Draw a straight line through these two points, which defines the linear transfer function 51. |
| Item 8. | Select period and ontime commands and turn noise diode 88 on. |
| Item 9. | Read $T_{BB+ND}$ by measuring signal 58. |
| Item 10. | Find $V_{OUT}$ for $T_{BB+ND}$. |
| Item 11. | Determine from the linear transfer function 51 the delta $T_{ND}$ which corresponds to delta $V_{ND}$. |
| Item 12. | Delta $T_{ND}$ is known for a known delta $V_{ND}$. |
| Item 13. | Repeat the above steps for the 31.4 GHz frequency. |

In detail, this procedure may be understood first by reference to FIG. 2A where the tipping curve 50 is shown as a plot of $V_{OUT}$ versus air mass. The 23.8 GHz Gunn diode 101 is turned on (see command 6.a). The $V_{OUT}$ data (step 2) is obtained by positioning the mirror 72 in the second position shown in FIG. 4 to obtain the $V_{zenith}$ reading at unity air mass. This is due in response to setting the elevation command 2.a. to "+90==Up". In Step 2, the various $V_{OUT}$ signals 33 from the radiometer 26 are obtained by controlling the position of the mirror 72 in response to the elevation commands (command 2.a.) in the computer program shown in Appendix A. At each different elevational angle, the new $V_{OUT}$ is determined and the resulting tipping curve is plotted. Next, in Step 3 the tipping curve is extrapolated to zero air mass to obtain a value for $V_{galactic}$. This corresponds to a known brightness temperature ($T_{galactic}$) of 2.7K.

The next step in the factory or preliminary calibration may be understood from FIG. 2B which shows the steps of calibrating the noise diode 88. This calibration is performed by drawing the first linear transfer function 51. Since, of course, the first linear transfer function 51 is by definition linear, it is drawn through two points. The first point is the ($V_{galactic}$, $T_{galactic}$) point that is plotted based on the tipping curve data. This is at 2.7K and is shown by point 118 in FIG. 2B.

Step 4 in the factory calibration is performed by the second or elevation command, which is set to "−90==Down". This causes the mirror 72 to move to the first position shown in FIG. 3. The signal 58 (FIGS. 7 and 8) is read in Step 5 to indicate $T_{BB}$. The period command and the ontime command are selected and a suitable RF signal integration time is selected. With the mirror 72 positioned "down" in response to command 6.d., the 23.8 GHz blackbody radiation signal 42 is reflected off the mirror 72 and is focused toward the common path 48 for processing by the circuit 107. Under the control of command 6.e., the radiometer output signal 33R1 is measured as $V_{BB}$, such that both the voltage and the temperature of a second point 119 (FIG. 2B) of the first linear transfer function 51 are known. For ease of description, it can be said that in Step 7 the first linear transfer curve 51 is plotted through the two points 118 and 119 and represents calibration data.

The calibration data represented by the first linear transfer function 51 is used to determine the effective delta T of the noise diode 88 (delta $T_{ND}$ In particular, in Step 8 by command 6.f., the noise diode 88 is turned on for a period "0" defined by the fourth ("0" or ontime) command (see command 3). With the noise diode 88 on for such period "0", in Step 9, command 5 is performed to read signal 58, representing $T_{BB+ND}$. In Step 10, the signal 33R2 is sensed to produce the $V_{BB+ND}$ value. These $V_{BB+ND}$ and $T_{BB+ND}$ values correspond to a point 120 in FIG. 2B. Delta $T_{ND}$, corresponding to delta $V_{ND}$, is then determined using the first linear transfer function 51, where:

delta $V_{ND} = V_{BB+ND} - V_{BB}$, and delta $T_{ND} = T_{BB+ND} - T_{BB}$.

Delta $T_{ND}$ is the effective and constant difference in the brightness temperature T resulting from the operation of the noise diode 88.

It should be understood that the operation of the noise diode 88 can be effected while the mirror 72 is in either of the first or second positions. To avoid potential problems with nonlinearity, in a preferred embodiment of the present invention the noise diode 88 is operated for calibration with the mirror 72 positioned in the second position and thus looking straight upwardly in the zenith position (see $T_{zenith}$ and $V_{zenith}$ in FIG. 2B). In either event, the delta $T_{ND}$ is determined by using the first linear transfer function 51.

Detailed Discussion of Realtime Calibration Method

Realtime calibration of the radiometer 26 can be effected without delays that have been experienced in the prior art in waiting, for example, for clear sky conditions. Instead, with the noise diode 88 having been calibrated before shipment and by using the realtime calibration method disclosed below, the radiometer 26 is calibrated each time an atmospheric reading is to be taken.

The radiometer 26 is calibrated during its normal broadband operation according to the sequence in the sixth, or read measurement channels, command. For producing the second linear transfer function 55 shown in FIG. 2C, after selecting the appropriate period command and ontime commands command to read $T_{BB}$. for example, command 6.a. is executed to turn on the 23.8 GHz Gunn diode 101. To produce the third linear transfer function 56, it should be understood that a corresponding command would be performed by turning on the Gunn diode 102 instead of the Gunn diode 101.

In response to command 6.b., the mirror 72 is located in the second position shown in FIG. 4. With the 23.8 GHz Gunn diode 101 on, the signal 33A is processed in response to command 6.c. to obtain $V_{33A}$ shown in FIG. 2C. Command 6.d. then sets the elevation command to "−90==Down" to receive the blackbody signals 42 and 43, for example. Then, in response to command 6.e., signal 33R1 is measured to determine $V_{BB}$ Since the thermometer 70 senses the temperature of the blackbody 54, both $V_{BB}$ and $T_{BB}$ are known and thus the point 59 in FIG. 2C is known. Next, in response to command 6.f., the noise diode control voltage 89 is applied to operate the noise diode 88. To control the circuit 35, the signal 112 would be applied. In response to command 6.g , the signal 33R2 is read and the $V_{BB+ND}$ voltage value is determined.

Commands 6.h. through 6.n. are performed to obtain data for the third linear transfer function 56.

As to the second linear transfer function 55, since the delta $T_{ND}$ is known, the $T_{BB+ND}$ value is known. As a result, the values of the voltage and temperature for the point 61 in FIG. 2C are known. In response to command 6.o., the processor 57 computes the points of the second linear transfer function 55 based on the points 59 and 61, so that the slope of the second linear transfer function 55 is known.

Realtime Atmospheric Sensing

When command 6.b is selected so as to position the mirror 72 in the second position (shown in FIG. 4), the broadband atmospheric signals 31 are admitted to the first section 39 of the housing 38. Such signals 31 include the 23.8 GHz signals 19. The signals 31 are reflected off the mirror 72 and through the aperture 46 and are focused by the lens 47 toward the common path 48. The portion of the signal 19 that is propagated through the wire grid polarizer 81 is propagated into the feed horn antenna 48 and then into the first waveguide 27 along the common path 28. The command 6.c. was executed so that the signal 33A was produced by the circuitry 107 and was applied to the processor 57. With the calibration data represented by the second linear transfer function 55 stored in the RAM 117 in the processor 57, the output voltage $V_{33A}$ derived from the signal 33A is used to determine the brightness temperature $T_{AWV}$ shown in FIG. 2C. The processor 57 performs command 6.p and obtains $T_{AWV}$ by using the output voltage $V_{33A}$ and the second linear transfer function 55. In this manner, the brightness temperature $T_{AWV}$ corresponding to the atmospheric water vapor in the atmosphere 29 from which the signal 31 was received is determined. As indicated above, such brightness temperature $T_{AWV}$ is representative of the water vapor content of such atmosphere 29.

In summary, since the tipping curve can be determined at the factory for example, the use of the radiometer 26 is not dependent on having a clear sky. Rather, since delta $T_{ND}$ is known, and since the blackbody 54 is used in realtime to obtain $V_{BB}$ and $T_{BB}$, the second linear transfer function 55 is obtained in realtime, independent of the availability of atmospheric conditions necessary for obtaining the tipping curve 50. The second linear transfer function 55 thus represents realtime calibration data.

By referring to Appendix A in conjunction with the above description, it may be understood that the 31.4 GHz signals 20 may be sensed and the third linear transfer function 56 used to determine the brightness temperature $T_{AL}$ that is used to represent the liquid content of the atmosphere 29 from which the signal 20 was received. Also, in a manner similar to that described above, each of the signals 113 through 116 for the respective 52.8, 53.8, 55.4 and 58.9 GHz frequencies in the V band is processed using the circuitry 35 to generate the various signals 37 corresponding to such frequency signals 113 through 116. Using such well-known techniques as are described in W. L. Smith's article, "Iterative Solution of the Radiative Transfer Equation for the Temperature and Absorbing Gas Profile of An Atmosphere", published in September, 1970, in *Applied Optics*, Vol. 9, No. 9, pp. 1993-1999, a temperature profile is generated and used to enhance the accuracy of the water substance measurements.

While the preferred embodiments have been described in order to illustrate the fundamental relationships of the present invention, it should be understood that numerous variations and modifications may be made to these embodiments without departing from the teachings and concepts of the present invention. Accordingly, it should be clearly understood that the form of the present invention described above and shown in the accompanying drawings is illustrative only and is not intended to limit the scope of the invention to less than that described in the following claims.

---

Serial Command Set:
1. I <if>    :initialize and test radiometer 26
2. E xxx <if>    :set elevation (degrees)
3. P xxx <if>    :set conversion period (microsec)
4. O xxx <if>    :set ontime (microsec)
5. R xx <if>    :read analog channel xx
6. M <if>    :read measurement channel
7. S <if>    :read status Detailed Description:
1. Initialize command:
This command locates the zero position sensors for the motor 74 and returns the mirror 72 to a known position (e.g. down). An internal self test is performed and the results are returned to the serial port.
  a. initialize circuitry 32, 35, 57 and 107
  b. test RAM 117
  c. +5, +15, -15, +12, 22-32V bus tests
  d. initialize motor 74
  e. report hardware options + results of test
2. Elevation command:
This argument, in floating point format, is the desired destination angle of the mirror 72 in degrees. The processor 57 converts the argument into units of steps and positions the motor 74 accordingly. When the processor 57 is finished controlling the motor 74, it returns the message "OK <cr><if>" to the serial port.
  a. −90==Down, 0==Azimuth, +90==Up, 180==Azimuth
3. Period command:
RF signal integration time (units of ms). Note: The RF channel is the only voltage for which this integration time is variable. All other voltages are measured by sampling for a fixed interval (33.333 ms or 100.0 ms).
4. Ontime command:
This command is used to specify the period for which the noise diode control signals 89 and 112 will be "on" during the variable part of the IF channel read.
  a. Pxxxx > = Oxxxx
5. Read analog channel command:
The specified channel is sampled for a predefined period and the results are returned in volts (sd.ddd<cr><if>).
6. Read measurement channels command:
  a. turn on 23.8 GHz Gunn diode local oscillator 101
  b. control motor 74 to locate mirror 72 in "up" or second position (FIG. 4).
  c. measure 23.8 GHz radiometer output voltage (signal 33A)
  d. control motor 74 to locate mirror 72 in "down" or first position (FIG. 3).
  e. measure 23.8 GHz radiometer output voltage (signal 33R1)
  f. turn on noise diode 88
  g. measure 23.8 GHz radiometer output voltage (signal 33R2)
  h. turn off 23.8 GHz Gunn diode 101 and turn on 31.4 GHz Gunn diode 102
  i. measure 31.4 (GHz radiometer output voltage (signal 34R2)
  j. turn off noise diode 88
  k. measure 31.4 GHz radiometer output voltage (signal 34R1)
  l. control motor 74 to locate mirror 72 in "up" or second position (FIG. 4)
  m. measure 31.4 GHz radiometer output voltage (signal 34A)
  n. turn off 31.4 GHz Gunn diode local oscillator 102

-continued o. obtain second linear transfer function 55
p. use function 55 and $V_{33A}$ from command 6.c to obtain $T_{AWV}$
7. Read status command:
At any time the radiometer 26 can be pulled over the serial bus to determine its general status. The two possible responses are "BUSY <cr><if>" to indicate that some command is being executed, and "READY <cr><if>" to indicate that the radiometer 26 can begin executing a new command.

What is claimed is:

1. A multi-channel, passive microwave radiometer for determining the water vapor content and the liquid content in the atmosphere, comprising:
    antenna means for receiving atmosphere signals having frequencies in two separate ITU protected bands, a first of which frequencies being above a given frequency of relative maximum water vapor absorption and a second of which frequencies being near a relative minimum in the water vapor absorption spectra; and
    a single radiometer responsive alternately to said received atmospheric signals from said antenna means at the first frequency and at the second frequency for generating output signals alternately representing such water vapor and such liquid content in the atmosphere from which such atmospheric signals were received.

2. A multi-channel, passive radiometer according to claim 1, wherein:
    the first frequency is about 23.8 GHz and the second frequency is about 31.4 GHz.

3. A multi-channel, passive radiometer according to claim 1, wherein:
    said separate ITU bands are in the ranges of 23.60 to 24.00 GHz and 31.3 to 31.5 GHz.

4. A multi-channel, passive radiometer according to claim 1, wherein:
    said amount of said relative maximum absorption varies with atmospheric pressure and wherein there is a crossover frequency lower than and a crossover frequency higher than that corresponding to said given frequency of maximum absorption, at each said crossover frequency said absorption being relatively independent of atmospheric pressure, said first frequency being about the same as said higher crossover frequency.

5. A multi-channel passive radiometer for determining the water vapor content and the liquid content in the atmosphere, comprising:
    antenna means for receiving atmospheric signals having frequencies in the two separate ITU protected bands, a first of which frequencies being above a given frequency of relative maximum water vapor absorption and a second of which frequencies being near a relative minimum in the water vapor absorption spectra;
    radiometer means responsive to said received atmospheric signals at the first and second frequencies for generating output signals representing such water vapor and such liquid content in the atmospheric from which such atmospheric signals were received;
    said antenna means including unitary waveguide means for guiding to said radiometer means signals having said first frequency and signals having said second frequency, both of said first and second frequencies being within the band pass of said unitary waveguide means; and
    a single microwave lens for focusing said atmospheric signals at said first and second frequencies into said unitary waveguide means.

6. A multi-channel, passive radiometer according to claim 5, wherein:
    said microwave lens has a convex surface and said unitary waveguide means includes a narrow angular beam width horn for guiding said focused signals from said microwave lens.

7. A multi-channel radiometer according to claim 1 for additionally measuring atmospheric temperature, wherein said atmospheric signals also include signals in the V band, further comprising:
    said antenna means is also effective to receive said V band signals and includes means interposed between the entrance aperture to said antenna means and said radiometer for diverting a wideband portion of said atmospheric signals; and
    a second radiometer responsive to said diverted signals in said V band for generating additional output signals representing the temperature of said atmospheric water vapor and liquid.

8. A multi-channel, passive microwave radiometer for determining the water vapor content and the liquid content in the atmosphere, wherein the microwave absorption coefficients of water vapor and liquid vary with frequency and wherein attenuation vs. frequency curves for water vapor at different altitudes each have a peak and cross each other at first and second pressure invariant frequencies, a first pressure invariant frequency being above the frequency corresponding to such peaks, comprising:
    a single antenna for receiving atmospheric signals having said first frequency and a third frequency, said first frequency being substantially in one of two separate ITU protected bands, said third frequency being substantially in the other of said ITU bands and being near a relative minimum in the water vapor absorption spectra; and
    a single radiometer responsive alternately to said received atmospheric signals at the first frequency and at the third frequency for generating successive output signals representing such water vapor content and such liquid content in the atmosphere from which such atmospheric signals were received.

9. A multi-channel, passive microwave radiometer for determining the water vapor content and the liquid content in the atmosphere, comprising:
    unitary waveguide means for guiding such microwave signals as are received from the atmosphere and as have first and second microwave frequencies, said first frequency being above the microwave frequency of relative maximum water vapor absorption, said second frequency being near a relative minimum in the microwave water vapor absorption spectrum; and
    means responding alternately to said first and second frequency signals from said unitary waveguide means for generating first and second output signals representing respectively the water vapor content and the liquid content of the atmosphere from which said microwave signals were received.

10. A multi-channel radiometer according to claim 9, wherein:

said generating means includes mixing means for receiving said first and second frequency signals from said waveguide means and for receiving selected signals having said first and second frequencies, said mixing means providing an output that selectively represents only said first frequency signal or only said second frequency signal.

11. A passive microwave radiometer, comprising:

feed horn means having a relatively small area for receiving microwave signals having first and second frequencies, said first frequency being above the frequency of relative maximum water vapor absorption and said second frequency being near a relative minimum in the water vapor absorption spectra;

means for receiving broadband microwave signals and for focusing into said feed horn means such of said signals as have said first and second frequencies;

unitary waveguide means for guiding such microwave signals as are received from said feed horn means and as have said first and second microwave frequencies; and means for selectively processing said first and second frequency signals from said unitary waveguide means to selectively generate first and second output signals representing respectively the water vapor content and the liquid content of the atmosphere from which said microwave signals were received.

12. A radiometer according to claim 11, further comprising:

means between said feed horns means and said focusing means for absorbing the side lobes of said signals having said first and second frequencies.

13. A radiometer according to claim 11, further comprising:

second waveguide means operatively connected to said receiving means for guiding broadband microwave signals in said V band;

grid means located between said focusing means and said feed horn means for directing a portion of said signals received by said receiving means into said second waveguide means; and means for processing said V band signals from said second waveguide means to generate output signals representing the temperature of the atmosphere from which said signals were received.

14. A radiometer according to claim 11. further comprising:

said receiving means having an input aperture for receiving microwave signals;

blackbody means mounted adjacent said input aperture of said receiving means for emitting known blackbody microwave signals having frequencies in the K and V bands; and means for selectively directing into said input aperture of said receiving means microwave signals from the atmosphere and from said blackbody means so that said blackbody signals are propagated through the same length of each of said receiving means, said feed horn means and said unitary waveguide means as said first and second signals are propagated to render said blackbody signals effective to form an accurate reference for measuring the K and V band atmospheric signals at said first and second frequencies.

15. A radiometer according to claim 14, wherein: said blackbody means includes:

a plate;

a blackbody material on one side of said plate; and means surrounding said plate and said blackbody material isothermal as the temperature thereof varies in response to changes in the local ambient temperature.

16. A radiometer according to claim 15, further comprising:

means for housing said feed horn means, said receiving means. said unitary waveguide means and said processing means electromagnetically but not thermally isolated from the local ambient atmosphere so that the temperature of said above-referenced means varies with that of the local ambient atmosphere, said housing means having a microwave signal window for admitting said signals to said directing means for selective input to said receiving means.

17. A radiometer according to claim 14, further comprising:

cross coupler means operatively coupled to said unitary waveguide means;

unitary noise diode means coupled to said cross coupler means for supplying noisy microwave signals to said waveguide means; and control means for causing said directing means to direct said blackbody signals to said receiving means so that said processing means produces a first known reference, said control means then causing said diode means to operate so that said noisy signals are added to said blackbody signals in said waveguide means to render said processing means effective to produce a second known reference.

18. A radiometer according to claim 17, wherein:

said control means causes said directing means to cycle so that upon obtaining said first and second known references said diode means is rendered inoperative and said atmospheric signals are propagated through said unitary waveguide means; and said processing means generates said first and second output signals by using said atmospheric signals at said first and second frequencies with said first and second known references.

19. A multi-channel, passive microwave radiometer for determining at least one selected characteristic of the atmosphere comprising;

housing means for containing said radiometer, said housing means having a first section and a microwave transparent window for admitting microwave signals from the atmosphere to said first section said housing means having a second section adjacent said first section;

blackbody means in said first section of said housing means adjacent said window for emitting blackbody microwave signals in the spectral region corresponding to said selected characteristics;

signal selecting means for directing either said blackbody microwave signals or said atmospheric microwave signals into said second section of said housing means; and antenna means in said second section of said housing means for selectively receiving said blackbody microwave signals or said microwave signals.

20. A multi-channel, passive microwave radiometer according to claim 19, further comprising:

waveguide means having a first section for propagating selected ones of said atmospheric signals and said blackbody signals received from said antenna means;

signal processing means responsive to said blackbody signals for generating a first reference signal; and means for adding a predetermined noise signal to said blackbody signals in said waveguide means to cause said signal processing means to generate a second reference signal;

said first and second reference signals forming realtime calibration data.

21. A multi-channel radiometer according to claim 20, further comprising:

means for controlling an operational cycle of said radiometer to initially cause said signal selecting means to select said blackbody signals so that they are propagated by said waveguide means;

said control means being effective in another portion of said operational cycle to cause said signal selecting means to select said atmospheric signals and to cause said adding means to become inoperative so that said first section of said waveguide means propagates said selected atmospheric signals to said signal processing means without said added noise signals; and said signal processing means being responsive to said atmospheric signals for generating a first output and using said first output with said realtime calibration data to generate a second output representative of said selected characteristic of said atmosphere.

22. A radiometer according to claim 21 for determining at least two selected characteristics of the atmosphere, a first of said characteristics being water vapor content and the second being liquid content, further comprising:

said blackbody signals in said spectral region corresponding to said first and second characteristics;

said first section of said waveguide means being a unitary waveguide for propagating signals having selected frequencies, a first of such frequencies being above a given frequency of relative maximum water vapor absorption and being in a first ITU band and a second of said frequencies being near a relative minimum in the water vapor absorption spectra and being in a second ITU band;

said control means being effective to initiate a first operational cycle by selecting from said unitary waveguide signals having said first frequency, said control means in said first operational cycle then being effective to cause said selecting means to successively select said blackbody signals and said atmospheric signals and to cause said adding means to operate so that second output of said processing means represents the water vapor content of the atmosphere from which said atmospheric signals are received;

said control means also being effective to initiate a second operational cycle by selecting said second frequency signals so that in said second cycle said second output of said processing means represents the liquid content of the atmosphere from which said atmospheric signals are received.

23. A radiometer according to claim 22 for also determining the temperature of the atmosphere from which said atmospheric signals are received, further comprising:

said selected spectral region of said blackbody means including the V band of atmospheric signals;

said waveguide means having a second section for propagating said V band signals received from said antenna means;

said processing means being responsive to said blackbody signals in said V band for generating a third reference signal and being responsive to said added blackbody signals in said V band and to said noise signal for generating a fourth reference signal, said third and fourth reference signals forming realtime temperature calibration data; and in response to said selecting means selecting said atmospheric signals, said processing means being effective to respond to said V band signals from said second waveguide section for generating a third output and using said third output with said temperature calibration data to generate a third output signal representative of said temperature of said atmosphere.

24. A method of determining the water vapor content and the liquid content in the atmosphere, comprising the steps of:

receiving atmospheric signals having frequencies substantially in two separate ITU protected bands, a first of which frequencies being above a peak frequency of relative maximum water vapor absorption and at a frequency at which attenuation by water vapor is substantially pressure invariant and a second of which frequencies is near a relative minimum in the water vapor absorption spectra; and in response to said received atmospheric signals at said first and second frequencies, generating output signals representing such water vapor and such liquid content in the atmosphere from which such atmospheric signals were received.

25. The method according to claim 24, wherein:

said amount of said relative maximum absorption varies with atmospheric pressure and wherein there is a frequency lower than and a frequency higher than that corresponding to said maximum absorption, at said lower and higher frequencies said absorption being relatively independent of atmospheric pressure, said first frequency being about the same as said higher frequency.

26. The method according to claim 24, wherein:

said separate ITU bands are in the ranges of 23.60 to 24.00 GHz and 31.3 to 31.5 GHz.

27. The method according to claim 24, wherein:

said first frequency is about 23.8 GHz and said second frequency is about 31.4 GHz.

28. The method according to claim 23, wherein said atmospheric signals at said first and second frequencies are guided in the same waveguide prior to being used to generate said output signals; and said atmospheric signals at said first and second frequencies are focused into said waveguide.

29. A method of determining the water vapor content and the liquid content in the atmosphere, comprising the steps of:

guiding in a single waveguide both such microwave signals as are received from the atmosphere and as have first and second microwave frequencies, said first frequency being above the microwave frequency of relative maximum water vapor absorption, said second frequency being near a relative minimum in the microwave water vapor absorption spectra; and alternately feeding said first and second frequency signals from said single waveguide to a common radiometer to generate first and second output signals representing respectively and successively the water vapor content and the liquid content of the atmosphere from which said microwave signals were received.

30. A method of determining the water vapor content and the liquid content in the atmosphere, comprising the steps of:

guiding in a common path both such microwave signals as are received from the atmosphere and as have first and second microwave frequencies, said first frequency being above the microwave frequency of relative maximum water vapor absorption, said second frequency being near a relative minimum in the microwave water vapor absorption responding alternately to said first and second frequency signals in said common path to generate first and second output signals representing respectively the water vapor content and the liquid content of the atmosphere from which said microwave signals were received;

mixing said first and second frequency signals from said common path and successive signals having said first frequency and then said second frequency to provide an output that successively represents only said first frequency signal and only said second frequency signal; and after each such mixing performing said generating step in response to said output.

31. A method of generating first and second output signals representing respectively the water vapor content and the liquid content of the atmosphere, comprising the steps of:

receiving microwave signals having first and second frequencies, said first frequency being above the frequency of relative maximum water vapor absorption and said second frequency being near a relative minimum in the water vapor absorption spectra;

using a lens for focusing said signals having said first and second frequencies toward a common waveguide; and using a single radiometer to successively process said first and second frequency signals from said common waveguide from which said microwave signals were received.

32. A method of determining at least one selected characteristic of the atmosphere, comprising the steps of:

admitting microwave signal from the atmosphere into a defined volume;

emitting into said volume blackbody microwave signals in the spectral region corresponding to said selected characteristic, said emitting alternating with such said admitting;

selecting ones of said atmospheric signals and said blackbody signals from said volume and propagating said selected signals along a common path;

generating a first reference signal in response to said blackbody signals in said common path;

adding a predetermined noisy signal to said blackbody signals in said common path to generate a second reference signal, said first and second reference signals forming calibration data;

when said atmospheric signals are propagated in said common path, causing said noisy signal to stop so that said common path propagates said selected atmospheric signals without said added noisy signal;

in response to said atmospheric signals, generating a first output; and comparing said first output to said calibration data to generate a second output representative of said selected characteristic of said atmosphere.

33. The method according to claim 32 for determining at least two selected characteristics of the atmosphere, a first of said characteristics being water vapor content and the second being liquid content, further comprising the steps of:

providing said selected spectral region of said blackbody means to correspond to said first and second characteristics;

propagating in said common path signals having frequencies in two separate ITU protected bands, a first of said signals having a frequency above a given frequency of relative maximum water vapor absorption and a second of said signals having a frequency near a relative minimum in the water vapor absorption spectrum;

initiating a first operational cycle by generating said first and second reference signals from said blackbody signals that just precede said first frequency atmospheric signals;

selecting from said common path said signals having said first frequency;

using said first frequency atmospheric signals with the calibration data derived from said first and second reference signals to obtain said second output representing the water vapor content of the atmosphere from which said atmospheric signals are received;

34. A portable, microwave radiometer for indicating the water vapor content, the liquid content and the temperature of the atmosphere, comprising:

a housing having first and second sections, each of said sections having a top and a bottom, said top of said first section being formed from a microwave signal—transparent window adapted to admit atmospheric microwave signals in the K and V bands to said first section;

a blackbody mounted inside said first section on the bottom thereof, said blackbody being effective to emit known microwave signals in the K and V bands;

a microwave signal mirror;

means for mounting said mirror between said top and said bottom in said first section of said housing for movement into a first position for reflecting only said blackbody signals into said second section and into a second position for reflecting only said atmospheric signals into said second section;

means having a central axis and being received in said second section of said housing adjacent said first section, said means being designed for focusing microwave signals having 23.8 GHz and 31.4 GHz frequencies toward a common path along said central axis and within said housing;

a cylindrical microwave signal collar having a relatively small diameter and being received in said second section, said collar having a second axis coextensive with said central axis of said focusing means, said collar having a material therein for absorbing side lobes of said focused microwave signals;

a horn mounted along said second axis for receiving said 23.8 GHz and 31.4 GHz focused signals;

a first waveguide coupled to said horn, said first waveguide being effective to propagate both said 23.8 GHz and 31.4 GHz signals along said common path;

a grid polarizer in said collar between said horn and said focusing means for deflecting some of said focused signals at an angle relative to said central axis, said deflected signals being at least in the V band;

a second waveguide for receiving and propagating said deflected V band signals;

heterodyne means for temporally separating said 23.8 GHz signal from said 31.4 GHz signal to form successive intermediate signals representing said 23.8 GHz and said 31.4 GHz signals; and means for separately processing each of said intermediate signals and said V band signals from said second waveguide for generating a first output signal representing said water vapor content, a second output signal representing said liquid content and a third output signal representing said temperature.

35. A portable, microwave radiometer according to claim 34 further comprising:

said housing being thermally conductive;

said first and second waveguide being permitted to drift at various temperatures according to the amount of thermal energy in said housing and to the amount of microwave energy admitted to said housing; and thermal insulation covering said blackbody so that the temperature thereof is substantially isothermal as thermal energy is transferred across such insulation to said blackbody.

36. A radiometer according to claim 35, further comprising:

means received under said insulation for indicating the temperature of said blackbody.

37. A radiometer according to claim 34, further comprising:

a noise diode adapted to generate a known noisy microwave signal;

means for attenuating said noisy signal at 23.8 a third waveguide cross-coupled to said first waveguide for propagating said attenuated noisy signal to said first waveguide;

control means for moving said mirror into said first position and causing said heterodyne means to first form said intermediate signal at about 23.8 GHz so that said blackbody signal at about 23.8 GHz is fed to said processing means;

said control means being effective to cause said noise diode to operate to add said known noisy signal to said intermediate blackbody signal fed to said processing means;

means responsive to said intermediate blackbody signal and to the sum of said intermediate blackbody and said noisy signal for generating signal versus temperature data for said 23.8 GHz signals;

said control means being effective to move said mirror into said second position while said intermediate signals are still at 23.8 GHz so that said 23.8 GHz atmospheric signal is fed to said processing means;

said processing means including means for using said 23.8 GHz atmospheric signal with said signal versus temperature data to generate said first output signal;

said control means being effective to cause said heterodyne means to form said intermediate signal at about 31.4 GHz and to cause said mirror to return to said first position so that said blackbody signal at about 31.4 GHz is fed to said processing means;

said control means being effective to cause said noise diode to operate to add said known noisy signal to said intermediate blackbody signal at 31.4 GHz fed to said processing means;

means responsive to said intermediate blackbody signal and the sum of said 31.4 GHz intermediate blackbody and noisy signals for generating signal versus temperature data for said 31.4 GHz signals;

said control means being effective to move said mirror into said second position while said intermediate signals are still at 31.4 GHz so that said 31.4 GHz atmospheric signal is fed to said processing means; and said processing means including means for using said 31.4 GHz atmospheric signal with said last mentioned signal versus temperature data to generate said second output signal.

* * * * *